(12) United States Patent
Ooi et al.

(10) Patent No.: US 8,399,706 B2
(45) Date of Patent: Mar. 19, 2013

(54) CHIRAL TETRAAMINOPHOSPHONIUM SALTS, CATALYST FOR ASYMMETRIC SYNTHESIS AND METHOD FOR PRODUCING CHIRAL β-NITROALCOHOL

(75) Inventors: Takashi Ooi, Nagoya (JP); Daisuke Uraguchi, Nagoya (JP)

(73) Assignees: Mitsui Chemicals, Inc., Tokyo (JP); National University Corporation Nagoya University, Aichi-Ken (JP)

( * ) Notice: Subject to any disclaimer, the term of this patent is extended or adjusted under 35 U.S.C. 154(b) by 722 days.

(21) Appl. No.: 12/212,243

(22) Filed: Sep. 17, 2008

(65) Prior Publication Data

US 2009/0131716 A1 May 21, 2009

(30) Foreign Application Priority Data

Nov. 21, 2007 (JP) ................................. 2007-302281

(51) Int. Cl.
*C07F 9/547* (2006.01)
*C07C 27/10* (2006.01)

(52) U.S. Cl. ......................................... 564/13; 568/700
(58) Field of Classification Search .................... 564/13; 568/700
See application file for complete search history.

(56) References Cited

FOREIGN PATENT DOCUMENTS

JP 2005-272339 A 10/2005
JP 2006-036737 A 2/2006

OTHER PUBLICATIONS

Daisuke Uraguchi et al., "Chiral Tetraaminophosphonium Salt-Mediated Asymmetric Direct Henry Reaction," J. Am. Chem. Soc., 2007, pp. 12392-12393, vol. 129, No. 51, ACS Publications.
Claudio Palomo et al., "Recent Advances in the Catalytic Asymmetric Nitroaldol (Henry) Reaction," Eur. J. Org. Chem., Microreview, 2007, pp. 2561-2574, Wiley-VCH Verlag GmbH & Co. KGaA, Weinheim.
Yoshihiro Sohtome et al., "Diastereoselective and Enantioselective Henry (Nitroaldol) Reaction Utilizing a Guanidine-Thiourea Bifunctional Organocatalyst," Eur. J. Org. Chem., Short Communication, 2006, 2894-2897, Wiley-VCH Verlag GmbH & Co. KGaA, Weinheim.
Palanichamy Ilankumaran et al., "Synthesis of Chiral Nonionic Superbases Based on Iminophosphoranes," Heteroatom Chemistry, Rapid Communication, 2000, pp. 251-253, vol. 11, No. 4, John Wiley & Sons, Inc.
Mathieu Sauthier et al., "Palladium(II) Complexes of Chiral 1,2-Diiminophosphoranes: Synthesis, Structural Characterization, and Catalytic Activity for the Allylic Alkylation," Organometallics, 2000, pp. 553-562, vol. 19, No. 4, American Chemical Society.
Uwe Köhn et al., "A New Class of Chiral Phosphazene Bases: Synthesis and Characterization," Eur. J. Org. Chem., Full Paper, 2006, pp. 4128-4134, Wiley-VCH Verlag GmbH & Co. KGaA, Weinheim.
Jean Michel Brunel et al., "First lminodiazaphospholidines with a Stereogenic Phosphorus Center, Application to Asymmetric Copper-Catalyzed Cyclopropanation," J. Am. Chem. Soc., 1999, pp. 5807-5808, vol. 121, No. 24, American Chemical Society.
Kazuaki Ishihara et al., "Synthesis of $C_3$ Symmetric, Optically Active Triamidoamine and Protetraazaphosphatrane," J. Org. Chem., 1998, pp. 5692-5695, vol. 63, No. 16, American Chemical Society.
Xiaodong Liu et al., "P[$S,S,S$)-PhHMeCNCH$_2$ CH$_2$ ]$_3$ N: A New Chiral$^{31}$ P and $^1$H NMR Spectroscopic Reagent for the Direct Determination of $ee$ Values of Chiral Azides," J. Org. Chem., 2000, pp. 701-706, vol. 65, No. 3, American Chemical Society.

*Primary Examiner* — Porfirio Nazario Gonzalez
(74) *Attorney, Agent, or Firm* — Buchanan Ingersoll & Rooney PC

(57) ABSTRACT

A chiral tetraaminophosphonium salt represented by formula (1) and a method for producing chiral β-nitroalcohol comprising reacting an aldehyde or a ketone and a nitroalkane in the presence of the chiral tetraaminophosphonium salt represented by formula (1) and a base, or in the presence of a conjugated base of the chiral tetraaminophosphonium salt represented by formula (1):

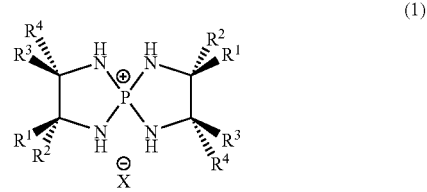

(1)

wherein $R^1$ to $R^4$ are independently a hydrogen atom or a monovalent hydrocarbon group; and, $R^1$ and $R^2$ are different groups or $R^3$ and $R^4$ are different groups.

8 Claims, 12 Drawing Sheets

CHIRAL TETRAAMINOPHOSPHONIUM SALTS, CATALYST FOR ASYMMETRIC SYNTHESIS AND METHOD FOR PRODUCING CHIRAL β-NITROALCOHOL

INCORPORATION BY REFERENCE

The disclosure of Japanese Patent Application No. 2007-302281 filed on Nov. 21, 2007 including the specification, drawings and abstract is incorporated herein by reference in its entirety.

BACKGROUND OF THE INVENTION

1. Field of the Invention

The present invention relates to a chiral tetraaminophosphonium salt, a catalyst for asymmetric synthesis comprising this chiral tetraaminophosphonium salt or conjugated base thereof, and a method for producing chiral β-nitroalcohols using this chiral tetraaminophosphonium salt or conjugated base thereof.

2. Related Art

β-nitroalcohols are widely used as synthesis intermediates for biologically active substances such as drugs and agricultural chemicals, and as raw materials for the synthesis of fine chemicals. The nitroaldol reaction (Henry reaction) involving a reaction between a nitroalkane and an aldehyde is a known method for synthesizing the β-nitroalcohol.

There is currently a desire for the development of methods for obtaining compounds having specific steric structures rather than unspecified target compounds, specifically, synthesis reactions that are stereoselective. For example, there are many chiral isomers having asymmetric carbon atoms in biologically active substances. Therefore, it is important to obtain chiral isomers having the desired absolute configuration. An example of the method for the production of chiral isomers is a method including synthesizing a racemic mixture and separating chiral isomers by optical resolution or the like. However, such methods have poor efficiency due to the requirement of chemical conversion and so on. Thus, developments also have been advancing in regard to asymmetric synthesis methods for selectively obtaining chiral isomers of β-nitroalcohols.

"Eur. J. Org. Chem. (2007) 2561-2574" describes the stereoselective synthesis of β-nitroalcohol by nitroaldol reaction using various catalysts.

JP-A-2005-272339 describes the methods for the production of chiral β-nitroalcohols by nitroaldol reaction in the presence of a chiral metal complex catalyst having cobalt ion or chromium ion.

JP-A-2006-36737 describes the methods for the production of chiral β-nitroalcohols by reacting an aromatic aldehyde and nitromethane in the presence of copper catalyst, and a copper compound and a chiral bisoxazoline compound or chiral diamine having a specific structure are allowed to come into contact to obtain a copper catalyst.

However, with methods for producing β-nitroalcohols by conventional nitroaldol reactions, the structures of the aldehydes and nitroalkanes that can be used are limited. In addition, there is currently a desire for the development of methods for producing β-nitroalcohols that have superior yields and stereoselectivity.

SUMMARY OF THE INVENTION

An object of the present invention is to provide a novel chiral tetraaminophosphonium salt which is useful in synthesis of β-nitroalcohols. In addition, another object of the present invention is to provide a catalyst for asymmetric synthesis that has high activity and capacity for steric control. Moreover, another object of the present invention is to provide a method for producing β-nitroalcohols that has superior yield and stereoselectivity using a carbonyl compound and a nitroalkanes having various structures.

The chiral tetraaminophosphonium salt of the present invention (hereinafter, referred to as "salt of the present invention") is represented by the general formula (1):

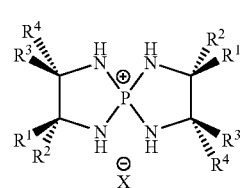

wherein $R^1$ to $R^4$ are independently a hydrogen atom or a monovalent hydrocarbon group; and, $R^1$ and $R^2$ are different groups or $R^3$ and $R^4$ are different groups.

The catalyst for asymmetric synthesis of the present invention (hereinafter, referred to as "catalyst of the present invention") comprises the salt of the present invention or a conjugated base thereof.

The method for producing β-nitroalcohol of the present invention (hereinafter, referred to as "method of the present invention") is one comprising reacting an aldehyde or a ketone and a nitroalkane in the presence of the salt of the present invention and a base, or in the presence of a conjugated base of the salt of the present invention.

The salt of the present invention is a novel compound that is different from conventional catalysts for synthesis of β-nitroalcohols. The salt and catalyst of the present invention have high activity and steric control in asymmetric synthesis such as β-nitroalcohol synthesis. The method of the present invention has superior yield and stereoselectivity (including enantioselectivity and diastereoselectivity) and can be widely utilized for carbonyl compounds and nitroalkanes having various structures.

DETAILED DESCRIPTION OF THE PREFERRED EMBODIMENTS

1. Chiral Tetraaminophosphonium Salt

Figure 1:
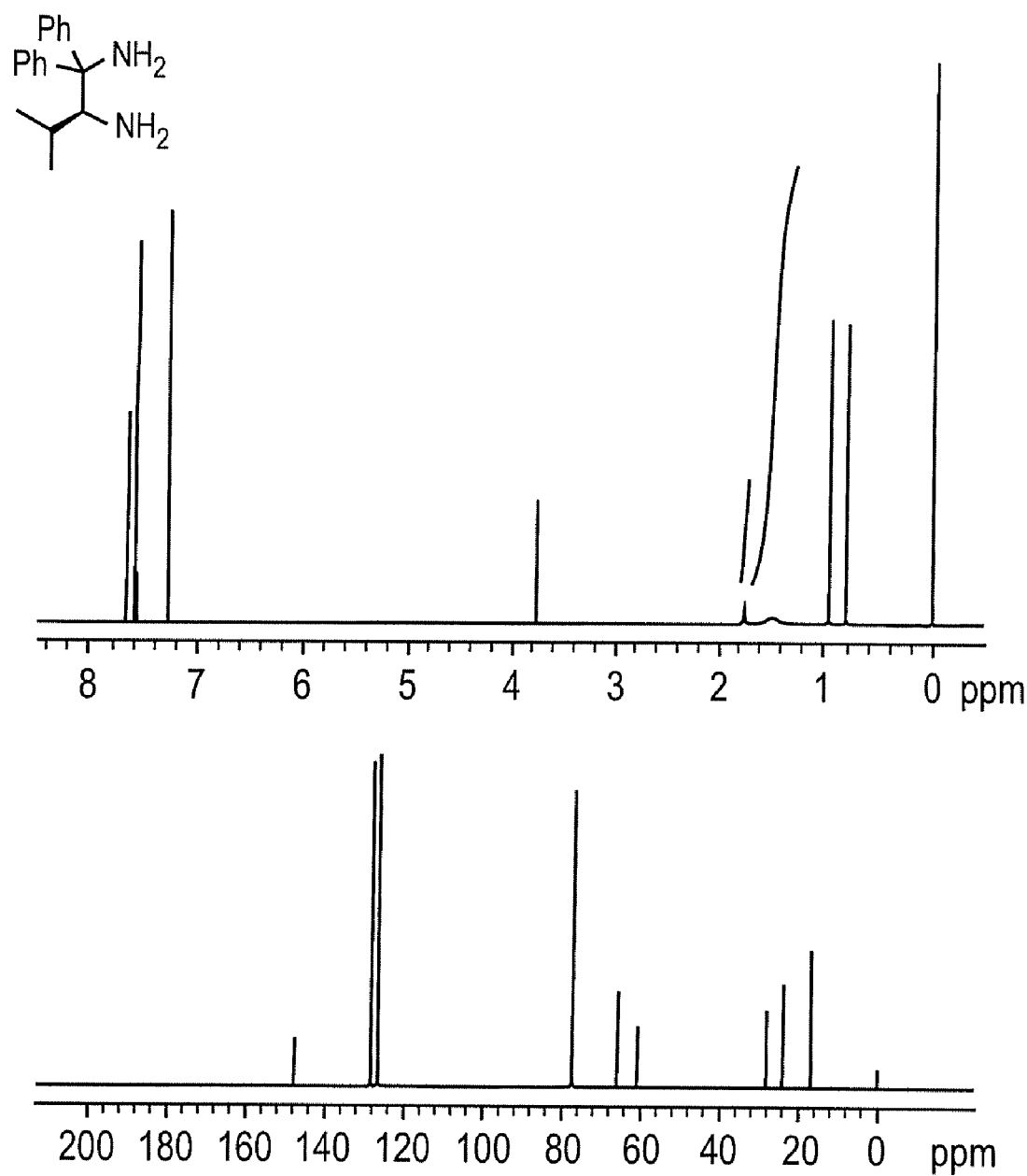
FIG. 1 shows $^1$H and $^{13}$C NMR spectra of 1,2-diamine (2a).

In the general formula (1), $R^1$ to $R^4$ are independently a hydrogen atom or a monovalent hydrocarbon group. There are no particular restrictions on the monovalent hydrocarbon group. As described below, the salt of the present invention can be used in asymmetric synthesis such as a method for producing β-nitroalcohols. Thus, it is preferable for the monovalent hydrocarbon group to not impede such asymmetric synthesis. Specific examples of the monovalent hydrocarbon group include an alkyl group, alkenyl group, alkynyl group, aryl group, arylalkyl group, arylalkenyl group and arylalkynyl group.

There are no particular restrictions on the structures of the alkyl group, alkenyl group and alkynyl group (hereinafter, referred to as "alkyl group or the like"). The alkyl group or the like may be a linear or branched. The alkyl group or the like may also have a chain structure or cyclic structure including a cycloalkyl group, cycloalkenyl group and cycloalkynyl group.

The alkyl group or the like may have one or more atoms other than carbon atoms and hydrogen atoms in its structure. The alkyl group or the like may also have one or two substituents having atoms other than carbon atoms and hydrocarbon atoms in its structure. In addition, the alkyl group or the like may have one or two atoms other than carbon atoms and hydrogen atoms in a chain structure or cyclic structure. Examples of the atom other than the above-mentioned carbon atom and hydrogen atom include one or more of oxygen atom, nitrogen atom and sulfur atom.

There are no particular restrictions on the number of carbons in relation to the alkyl group or the like. The number of carbon atoms of the alkyl group is normally 1 to 10, preferably 1 to 8, more preferably 1 to 6, further preferably 1 to 4, and particularly 1 to 3. The number of carbon atoms of the alkenyl group or alkynyl group is normally 2 to 10, preferably 2 to 8, more preferably 2 to 6, and particularly 2 to 4. When the alkyl group or the like is in a cyclic structure, the number of carbons of the alkyl group or the like is normally 4 to 12, preferably 4 to 10, more preferably 5 to 8, and particularly 6 to 8.

Specific examples of the alkyl group include methyl group, ethyl group, n-propyl group, i-propyl group, n-butyl group, i-butyl group, sec-butyl group, t-butyl group, pentyl group, isopentyl group, neopentyl group, hexyl group, heptyl group, octyl group and 2-ethylhexyl group. Specific examples of the cycloalkyl group include cyclopentyl group, cyclohexyl group, cycloheptyl group and 2-methyl cyclohexyl group. Examples of the alkenyl group include vinyl group, allyl group and isopropenyl group. Specific examples of the cycloalkenyl group include cyclohexenyl group.

There are no particular restrictions on the structures of the aryl group, arylalkyl group, arylalkenyl group and arylalkynyl group (hereinafter, referred to as "aryl group or the like"). The aryl group or the like may have one or more other substituents. For example, the aromatic ring in the aryl group or the like may have one or more other substituents. Consequently, cases are included not just in which an unsubstituted aryl group or the like is present, but also in which an aryl group is present that has substituents on the aromatic ring. The position of the substituents on the aromatic ring may be o-, m-, or p-position. Specific examples of the substituents include one or more of a halogen atom such as fluorine atom, chlorine atom and bromine atom, an alkyl group, an alkenyl group, an aryl group, a nitro group, a substituted amino group, and an alkoxy group.

There are no particular restrictions on the number of carbons in relation to the aryl group or the like. The number of carbon atoms of the aryl group or the like is normally 6 to 15, preferably 6 to 12, and more preferably 6 to 10.

Specific examples of the aryl group include an unsubstituted aryl group ($C_6H_5$—), an aryl group containing a trifluoromethyl group (o-, m-, or p-) ($CF_3$—$C_6H_4$—), tolyl group, ethylphenyl group, xylyl group, cumenyl group, mesityl group, methoxyphenyl group (o-, m-, or p-), ethoxyphenyl group (o-, m-, or p-), 1-naphthyl group, 2-naphthyl group and biphenyl group. Specific examples of the arylalkyl group include benzyl group, methoxybenzyl group (o-, m-, or p-), ethoxybenzyl group (o-, m-, or p-) and phenetyl group. Specific examples of the arylalkenyl group include styryl group and cinnamyl group.

There are no particular restrictions on the combinations of $R^1$ to $R^4$. However, $R^1$ and $R^2$ are different groups or $R^3$ and $R^4$ are different groups. Consequently, the salt of the present invention has at least two asymmetric carbon atoms. For example, $R^1$ and $R^2$ may be different groups, and $R^3$ and $R^4$ may be the same groups; or $R^1$ and $R^2$ may be the same groups and $R^3$ and $R^4$ may be different groups. Moreover, $R^1$ and $R^2$ may be different groups and $R^3$ and $R^4$ may be different groups. Regarding the combinations of $R^1$ to $R^4$, the various groups exemplified above may be used in suitable combinations as necessary.

A specific combination of $R^1$ to $R^4$ is one in which one of $R^1$ and $R^2$ is a hydrogen atom and $R^3$ and $R^4$ are aryl groups (e.g., unsubstituted aryl groups). When $R^3$ and $R^4$ are aryl groups, one of $R^3$ and $R^4$ may be an unsubstituted aryl group and the other may be a substituted aryl group. Alternatively, both $R^3$ and $R^4$ may be unsubstituted aryl groups or substituted aryl groups.

In the general formula (1), there are no particular restrictions on the type or valence of $X^-$ counter-ion. $X^-$ may be a conventionally monovalent or polyvalent anion. As described below, the salt of the present invention can be produced by allowing a 1,2-diamine compound having specific structure and a halogenated phosphorus compound to react. Thus, $X^-$ is ordinarily a halogen ion (e.g., $F^-$, $Cl^-$, $Br^-$, $I^-$). In addition, suitable ion exchange may be carried out as necessary in the present invention. In such a case, $X^-$ may be sulfate ion, hydrogen sulfate ion, carboxylate ion, phosphate ion, phosphite ion, phenoxide, borate ion, tetra-aryl borate ion, tetrafluoroborate ion, hexafluorophosphate ion, or the like.

When the carbon atom to which $R^1$ and $R^2$ are bonded in the general formula (1) is an asymmetric carbon atom, there are no particular restrictions on the steric structure of the site. The steric structure may be R- or S-forms.

Specific examples of the salt of the present invention include the following chiral tetraaminophosphonium salts represented by the general formula (1-1) and enantiomers thereof, the following chiral tetraaminophosphonium salts represented by the general formula (1-2) and enantiomers thereof.

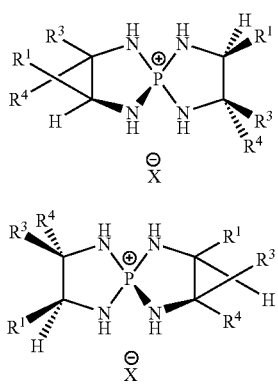

(1-1)

(1-2)

There are no particular restrictions on the method for producing the salt of the present invention. The salt of the present invention may be produced by reacting a halogenated phosphorus compound and the following 1,2-diamine compound represented by the general formula (1a). The 1,2-diamine compound may be chiral or racemic. When the 1,2-diamine compound is a racemic mixture, optical resolution or the like can be carried out after synthesis to obtain the salt of the present invention. The 1,2-diamine compound may be obtained from readily procurable amino acids. The amino acid may be D- or L-forms.

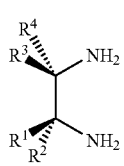

(1a)

2. Catalyst for Asymmetric Synthesis

The catalyst of the present invention comprises the salt of the present invention or conjugated base thereof. The "conjugated base" of the salt of the present invention is an iminophosphorane compound obtained by deprotonation of the salt of the present invention (e.g., a triaminoiminophosphorane). The catalyst of the present invention can lead asymmetric synthesis (e.g., β-nitroalcohol synthesis reaction) even if it is not a metal complex.

The catalyst of the present invention has no particular restrictions on its composition, provided that it contains the salt of the present invention or conjugated base thereof. The catalyst of the present invention can contain the salt of the present invention or conjugated base thereof, or may also contain both. In addition, the catalyst of the present invention may have a structure that comprises only the salt of the present invention or conjugated base thereof, but may also contain other components. Moreover, the salt of the present invention or conjugated base thereof may be a single type of optical isomer, but may also contain two or more different optical isomers.

There are no particular restrictions on the form of the catalyst of the present invention. The catalyst of the present invention may be present in a solvent or may be present as residue resulting from evaporation of the solvent. In addition, the catalyst of the present invention may not be isolated. The catalyst of the present invention may be used in β-nitroalcohol synthesis reaction in the form in which it has been produced. More specifically, after producing the catalyst of the present invention in a suitable solvent, the solution containing the catalyst of the present invention can be added to a reaction solvent for asymmetric synthesis reaction (e.g., β-nitroalcohol synthesis reaction). Alternatively, after generating the catalyst of the present invention in a suitable solvent, starting materials for asymmetric synthesis reaction are added to the reaction solvent, and the asymmetric synthesis reaction can then be carried out.

When the catalyst of the present invention is dispersed or dissolved in a solvent, there are no particular restrictions on the type of solvent. As described above, the catalyst of the present invention can be used directly in a prepared state for β-nitroalcohol synthesis reaction. Thus, the solvent is preferably the same as the solvent for β-nitroalcohol synthesis reaction or a solvent that has similar properties as this solvent. A polar organic solvent or nonpolar organic solvent may be used as the solvent. In addition, one or a mixture of two or more of the above solvents may be used.

The polar organic solvent may be a protic polar organic solvent or an aprotic polar organic solvent. The polar organic solvent is preferably an aprotic polar organic solvent. Examples of the polar organic solvent include THF, anisole, 1,4-dioxane, cyclopentyl methyl ether, an alcohol such as methanol, ethanol and allyl alcohols, and an ester compound such as ethyl acetate. In addition, the polar solvent may be an amide-based solvent such as DMF and NMP, a urea-based solvent such as DMPU, a phosphoric acid amide-based solvent such as HMPA, a nitrile-based solvent such as propionitrile, and a nitroalkane-based solvent such as nitromethane and nitroethane.

The nonpolar solvent may be an aliphatic organic solvent or an aromatic organic solvent. Examples of the aliphatic organic solvent include an alkane and a cycloalkane both having carbon atoms of 4 or more, preferably 5 or more. Specific examples of the aliphatic organic solvent include pentane, hexane, cyclohexane, heptane and octane. Examples of the aromatic organic solvent include benzene and toluene.

There are no particular restrictions on the type of asymmetric synthesis. Specific examples of the asymmetric synthesis include a synthesis of chiral β-nitroalcohols in which an aldehyde or ketone is reacted with a nitroalkane.

3. Method for Producing Chiral β-Nitroalcohol

Types and structures of the aldehyde and the ketone are not particularly restricted so long as β-nitroalcohols can be obtained. The following compound represented by the general formula (2) may be used as the aldehyde and ketone.

(2)

In the general formula (2), $R^7$ is a monovalent hydrocarbon group, and $R^8$ is a hydrogen atom or a monovalent hydrocarbon group. When $R^8$ is a hydrogen atom, the compound represented by the general formula (2) is an aldehyde, whereas when $R^8$ is a monovalent hydrocarbon group, the compound represented by the general formula (2) is a ketone.

Examples of the monovalent hydrocarbon group include an alkyl group, alkenyl group, alkynyl group, aryl group, arylalkyl group, arylalkenyl group and arylalkynyl group. Regarding types and structures of the alkyl group, alkenyl group, alkynyl group, aryl group, arylalkyl group, arylalkenyl group and arylalkynyl group, the explanation of $R^1$ to $R^4$ in the salt of the present invention can be applicable. In the case where $R^7$ and $R^8$ have an unsaturated bond, the number of the unsaturated bond is not particularly restricted.

When the compound represented by the general formula (2) is an aldehyde, $R^7$ can be an aryl group, polycyclic aromatic hydrocarbon group, aromatic heterocyclic group, or R—CH=CH— group (wherein R is a Y—CH=CH—, an aryl group, a polycyclic aromatic hydrocarbon group, or an aromatic heterocyclic group; and Y is a hydrogen atom or a monovalent hydrocarbon group). It is preferable for $R^7$ to be one of the above groups, because the catalyst of the present invention can have excellent enantioselectivity and diastereoselectivity for preparation of β-nitroalcohol from such aldehydes. Specific examples of the polycyclic aromatic hydrocarbon group include a naphthyl group such as 1-naphthyl group and 2-naphthyl group. Specific examples of the aromatic heterocyclic group include an aromatic heterocyclic group having an oxygen atom such as 2-furyl group.

When $R^7$ is an aryl group, polycyclic aromatic hydrocarbon group, or aromatic heterocyclic group, the aromatic ring may be optionally substituted with other functional groups. The other functional groups may be electron withdrawing groups or electron donating groups. Specific examples of the other functional groups include an alkyl group including linear and branched alkyl groups having carbon atoms of 1 to 4 such as methyl group and ethyl group, a halogen atom such as F, Cl and Br, an alkoxy group such as methoxy group and ethoxy group, a halogenated alkyl group such as trifluoromethyl group, nitro group, cyano group and carbonyl group. In addition, there are no particular restrictions on the positions of the other functional groups, and o-, m-, and p-positions may be used. The positions of the other functional groups are normally o- and p-positions. Specific examples of $R^7$ having other functional groups are aryl groups that are substituted with an alkyl group or a halogen atom at o- or p-positions.

The monovalent hydrocarbon group may contain one or more types of other functional groups or other atoms, provided that they do not impede the synthesis of β-nitroalcohol. Specific examples of other functional groups or other atoms include the other functional groups and other atoms cited in the description of $R^1$ to $R^4$ of the salt of the present invention.

The ketone may be an asymmetrical ketone or a symmetrical ketone. Examples of the symmetrical ketone include ketones wherein $R^7$ and $R^8$ are the same alkyl group, alkenyl group, or alkynyl group having carbon atoms of 1 to 5 and preferably 1 to 3 (e.g., acetone, diethyl ketone). Examples of the asymmetrical ketone include (1) ketones wherein $R^7$ is an alkyl group, alkenyl group or alkynyl group having carbon atoms of 1 to 5 and preferably 1 to 3 and $R^8$ is an alkyl group, alkenyl group or alkynyl group having carbon atoms of 1 to 5 and preferably 1 to 3 and that is different from $R^7$; and (2) ketones wherein $R^7$ is an alkyl group, alkenyl group or alkynyl group having carbon atoms of 1 to 5 and preferably 1 to 3 and $R^8$ is an aryl group, arylalkyl group or arylalkenyl group.

$R^7$ and $R^8$ may have an electron withdrawing group such as carbonyl group, alkoxycarbonyl group, aminocarbonyl group and halogenated alkyl group. In addition, $R^7$ and $R^8$ may also be electron withdrawing groups themselves, such as carbonyl group, alkoxycarbonyl group, aminocarbonyl group and halogenated alkyl group. The following compounds are examples of ketones wherein $R^7$ and $R^8$ are electron withdrawing groups.

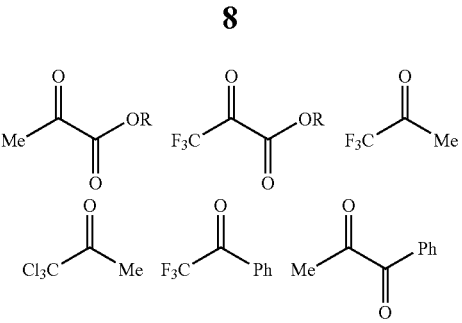

There are no particular restrictions on the combinations of $R^7$ and $R^8$. $R^7$ and $R^8$ may be the same or different. $R^7$ and $R^8$ may also bond together to form a ring.

There are no particular restrictions on the type and structure of the nitroalkane, provided that β-nitroalcohols can be produced. Examples of the nitroalkane include the following nitroalkane represented by the general formula (3). The "nitroalkane" may have a structure wherein the carbon atom to which the nitro group is bonded and the atom that is adjacent to this carbon atom is bonded by a saturated bond. Consequently, the "nitroalkane" may have an unsaturated bond in its chain, provided that it satisfies the above condition ($R^9$ and $R^{10}$ in the general formula (3) below may be a group having an unsaturated bond, such as alkenyl group and alkynyl group).

(3)

In the general formula (3), $R^9$ and $R^{10}$ each independently a hydrogen atom or a monovalent hydrocarbon group. Examples of the monovalent hydrocarbon group include an alkyl group, alkenyl group, alkynyl group, aryl group, arylalkyl group, arylalkenyl group and arylalkynyl group. Regarding structures of the alkyl group, alkenyl group, alkynyl group, aryl group, arylalkyl group, arylalkenyl group and arylalkynyl group, the explanation of $R^1$ to $R^4$ in the salt of the present invention can be applicable. The monovalent hydrocarbon group is preferably a saturated hydrocarbon group having carbon atoms of 1 to 5, and is particularly methyl group, ethyl group, n-propyl group and i-propyl group.

The monovalent hydrocarbon group may have one or more types of other functional group or other atom in its structure, provided that they do not impede synthesis of β-nitroalcohols of the present invention. Specific examples of other functional groups or other atoms include the other functional group and other atoms cited in the description of $R^1$ to $R^4$ of the salt of the present invention.

There are no particular restrictions on the combinations of $R^9$ and $R^{10}$. $R^9$ and $R^{10}$ may be the same or different groups. In addition, $R^9$ and $R^{10}$ may both be hydrogen atoms or either may be a monovalent hydrocarbon group. Moreover, one of $R^9$ and $R^{10}$ may be a hydrogen atom and the other may be a monovalent hydrocarbon group. Regarding combinations of $R^9$ and $R^{10}$, it is preferable for both to be hydrogen atoms or for one to be a hydrogen atom and the other to be a monovalent hydrocarbon group, specifically, a saturated hydrocarbon group having carbon atoms of 1 to 5 (more preferably, methyl group, ethyl group, n-propyl group, or i-propyl group). $R^9$ and $R^{10}$ may bond together to form a ring. When the ketone is a symmetrical ketone, the nitroalkane to be used is a nitroalkane wherein at least one of $R^9$ and $R^{10}$ is the monovalent hydrocarbon group, with $R^9$ and $R^{10}$ being different groups.

There are no particular restrictions on the ratio of the aldehyde or ketone and the nitroalkane for reaction. The ratio of the aldehyde or ketone and the nitroalkane (equivalent weight ratio) is normally 1:(0.1 to 20), preferably 1:(1 to 20), more preferably 1:(1 to 15), and particularly 1:(1 to 10). In the present invention, the solvent itself may be the nitroalkane.

The method of the present invention is carried out in the presence of the salt of the present invention and a base or in the presence of a conjugated base of the salt of the present invention. As described below, in the method of the present invention, it is thought that an iminophosphorane compound which is a conjugated base of the salt of the present invention (e.g., triaminoiminophosphorane) contributes to the reaction (this description is a supposition of the present inventors). Consequently, when the method of the present invention is carried out in the presence of the conjugated base of the salt of the present invention, it is not necessary for a base to be present.

There are no particular restrictions on the type of the base. The base, as described below, is thought to function to generate an iminophosphorane compound through extracting a hydrogen atom bonded to a nitrogen atom of the salt of the present invention (this description is a supposition of the present inventors). The base may be used an inorganic base or organic base. Specific examples of inorganic base include a metal hydride. Specific examples of organic base include an amine compound (e.g., primary, secondary, tertiary; such as guanidine and amidine), a metal alkoxide such as sodium methoxide, sodium ethoxide and potassium-t-butoxide, an alkyl metal compound such as butyl lithium, and a metal amide such as potassium hexamethyl disilazane. The base may be used singly or in combination of two or more types thereof. The base is preferably a metal alkoxide, an alkyl metal compound and a metal amide.

Examples of the metal that constitute the metal alkoxide, alkyl metal compound and metal amide include an alkali metal such as Na and K; an alkaline earth metal such as Ca; Al and Zn. Examples of the alkoxide constituting the metal alkoxide include a linear and branched alkoxy groups having carbon atoms of 1 to 5, preferably 1 to 4, such as methoxy group, ethoxy group, n-propoxy group, i-propoxy group and t-butoxy group.

In the method of the present invention, specific procedures are not particularly restricted, provided that production is carried out in the presence of the salt of the present invention and a base or in the presence of a conjugated base of the salt of the present invention. The method of the present invention may comprise producing the salt of the present invention, and then adding a base and a substrate to a solution containing the salt of the present invention without separating the salt of the present invention. Alternatively, the method of the present invention can be carried out by addition of the salt of the present invention, base, and substrate to a separately prepared solvent. Moreover, after the conjugated base of the salt of the present invention is generated by adding a base to a solution containing the salt of the present invention, and this material may then be used in the production method of the present invention. The description "in the presence of the salt of the present invention and a base or in the presence of a conjugated base of the salt of the present invention" simply refers to the state in which the salt of the present invention or the conjugated base of the salt of the present invention is present. This condition includes not only cases where the salt of the present invention is used, but cases where the catalyst of the present invention is used.

In the method of the present invention, there are no particular restrictions on the amount of the salt of the present invention or the conjugated base of the salt of the present invention for reaction. The amount of the salt of the present invention or the conjugated base of the salt of the present invention is normally in the range from 0.5 to 10 mol %, and preferably from 1 to 7 mol % with respect to the aldehyde or the ketone.

In the method of the present invention, there are no particular restrictions on the type of solvent. The solvent may be used a polar organic solvent or nonpolar organic solvent. Moreover, one type or a mixed solvent of two or more types may be used for the solvent.

The polar organic solvent may be a protic polar organic solvent or an aprotic polar organic solvent. The polar organic solvent is preferably an aprotic polar organic solvent. Examples of the polar organic solvent include THF, anisole, 1,4-dioxane, cyclopentyl methyl ether, an alcohol such as methanol, ethanol and allyl alcohols, and an ester compound such as ethyl acetate. In addition, the polar solvent may be an amide-based solvent such as DMF and NMP, a urea-based solvent such as DMPU, a phosphoric acid amide-based solvent such as HMPA, a nitrile-based solvent such as propionitrile, and a nitroalkane-based solvent such as nitromethane and nitroethane.

The nonpolar solvent may be an aliphatic organic solvent or an aromatic organic solvent. Examples of the aliphatic organic solvent include an alkane and a cycloalkane both having carbon atoms of 4 or more, preferably 5 or more. Specific examples of the aliphatic organic solvent include pentane, hexane, cyclohexane, heptane and octane. Further, examples of the aromatic organic solvent include benzene and toluene.

In the method of the present invention, there are no particular restrictions on the reaction conditions. The reaction conditions may be suitably adjusted in accordance with the type and structure of the starting materials, the structure of the β-nitroalcohol and the like. The reaction time is normally in the range from 3 to 48 hours, preferably 3 to 30 hours, more preferably 4 to 24 hours, and particularly 4 to 12 hours. The reaction temperature is normally in the range from −100° C. to 40° C., preferably −80° C. to 30° C., and more preferably −80° C. to 10° C.

Additionally, there are no particular restrictions on the reaction atmosphere in the method of the present invention. The present production may be carried out in an oxygen-free atmosphere or in oxygen gas atmosphere. The present production may also be carried out in nitrogen gas atmosphere or a rare gas atmosphere (e.g., helium gas, neon gas, argon gas).

After completion of the reaction, recovery and purification of the target β-nitroalcohol may be carried out by well-known methods including distillation, adsorption, extraction and recrystallization, or combinations of these methods. In addition, the target chiral isomer may be obtained by optical resolution or the like.

The syn-isomer and anti-isomer are conceivable isomeric structures of the β-nitroalcohol obtained by the method of the present invention (refer to the structures below). The β-nitroalcohol may be either one of the syn-isomer and anti-isomer, or a mixture of both. The salt and catalyst of the present invention have superior anti-selectivity. Thus, the β-nitroalcohol obtained by the method of the present invention is preferably an anti-isomer or a mixture containing a large quantity of an anti-isomer.

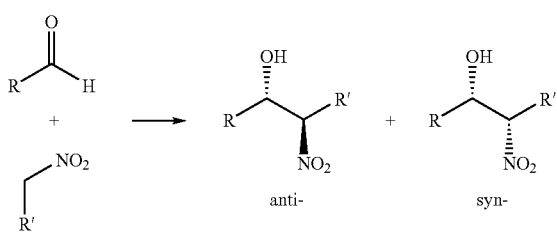

The reaction mechanism in the method of the present invention is thought as follows. Specifically, a hydrogen atom bonded to a nitrogen atom of the salt (3) of the present invention is extracted by a base such as potassium-t-butoxide, thereby generating an iminophosphorane (I). Next, an ionic pair (II) is formed between the iminophosphorane (I) and nitroalkane. Subsequently, the ion pair (II) and the aldehyde or the ketone react (in the reaction mechanism shown below, an aldehyde is used as an example), and a β-nitroalkane is generated, with regeneration of iminophosphorane (I). The reaction mechanism shown below and this description are suppositions of the present inventors. Consequently, the reaction mechanism shown below and this description are not ones restrict the present invention in any way, nor do they describe a main point that defines the present invention.

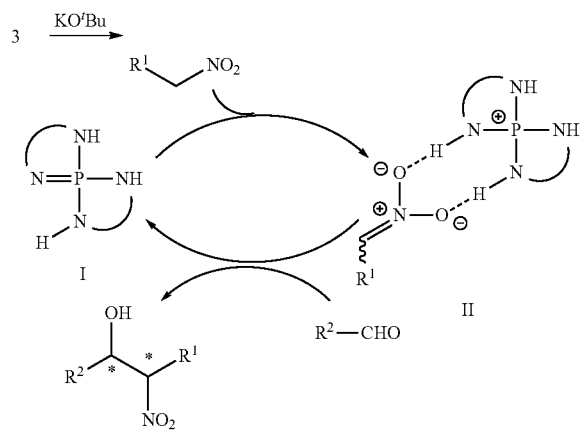

EXAMPLES

The present invention is described in detail below using examples. The present invention, however, is not restricted to the modes presented in the Examples. Embodiments of the present invention can undergo various modifications within the scope of the present invention in accordance with objectives and applications.

In the Examples, Infrared spectra were recorded on a "JASCO FT/IR-230 spectrometer". $^1$H-NMR spectra were recorded on a "Varian INOVA-500 (500 MHz) spectrometer". Chemical shifts are reported in ppm from the solvent resonance as the internal standard (CD$_3$OD; 3.31 ppm) or tetramethylsilane (0.0 ppm) resonance as the internal standard (CDCl$_3$). $^{13}$C-NMR spectra were recorded on a "Varian INOVA-500 (126 MHz) spectrometer" with complete proton decoupling. Chemical shifts are reported in ppm from the solvent resonance as the internal standard (CDCl$_3$; 77.16 ppm, CD$_3$OD; 49.0 ppm). $^{31}$P-NMR spectra were recorded on a "Varian Mercury-300BB (121 MHz) spectrometer" with complete proton decoupling. Chemical shifts are reported in ppm from H$_3$PO$_4$ (0.0 ppm) resonance as the external standard. $^{19}$F-NMR spectra were recorded on a "Varian Mercury-300BB (282 MHz) spectrometer". Chemical shifts are reported in ppm from benzotrifluoride (−64.0 ppm) resonance as the external standard. Optical rotations were measured on a "JASCO P-1020NS polarimeter". The high resolution mass spectra were conducted at the Research Center for Materials Science, Graduate School of Science, Nagoya University. Analytical thin layer chromatography (TLC) was performed on "Merck precoated TLC plates" (silica gel 60, GF$_{254}$, 0.25 mm). Flash column chromatography was performed on "silica gel 60" (spherical, 40-50 μm; Kanto Chemical Co., Inc.).

Data are reported as follows: chemical shift, integration, multiplicity (s=singlet, d=doublet, t=triplet, q=quartet, quin=quintet, brs=broad singlet) and coupling constants (Hz).

All reactions were carried out under an Argon (Ar) atmosphere in dried glassware. All substrate were purified by column chromatography or distillation prior to use. Toluene and tetrahydrofuran (THF) were supplied from Kanto Chemical Co., Inc. as "Dehydrated solvent system". Other simple chemicals were purchased and used as such.

1. Synthesis of Chiral Tetraaminophosphonium Salt (I)

The synthetic scheme for the chiral tetraaminophosphonium salt is shown below.

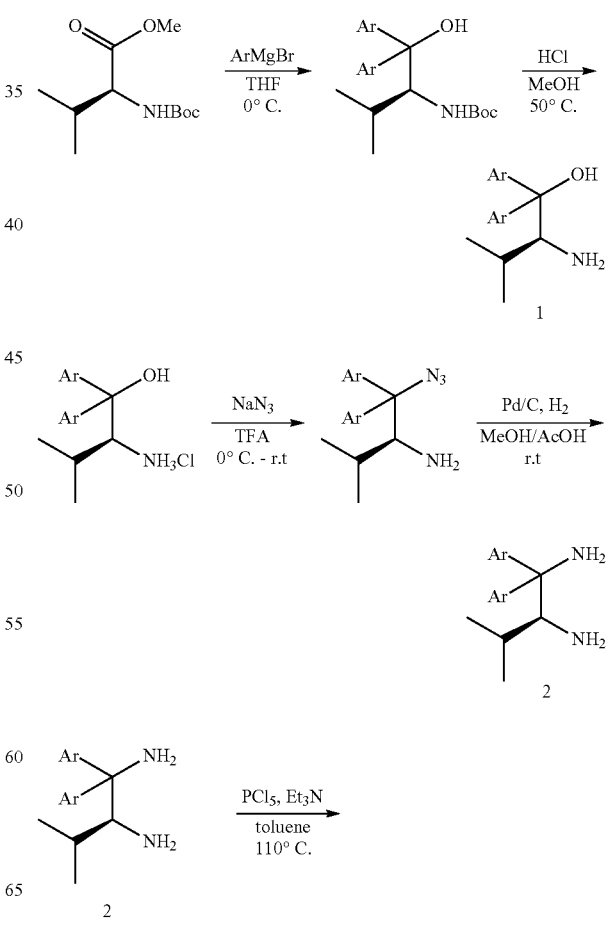

-continued

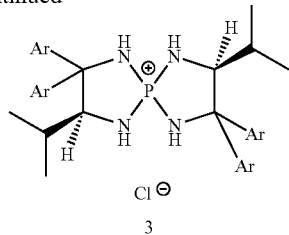

3

Yield
3a: 92%
3b: 63%
3c: 94%
3d: 99%

1a, 2a, 3a: Ar = Ph
1b, 2b, 3b: m-Xylyl
1c, 2c, 3c: p-Tolyl
1d, 2d, 3d: p-CF$_3$—C$_6$H$_4$ A solution of Boc-L-Val-OMe (10 mmol) in THF was added to a slurry of PhMgBr in THF (ca. 1M, 50 mL, 5 equiv) at 0° C. The resulting mixture was stirred at 0° C. for 1 hour and poured into ice-cooled aqueous NH$_4$Cl. The phases were separated and the aqueous phase was extracted with ethyl acetate twice, and the ethyl acetate phase was added to the organic phase. The combined organic phase was dried over Na$_2$SO$_4$ and filtered. The concentrated crude residue was treated with 30 mL of 1M methanolic HCl at 50° C. for 3 hours. Then, MeOH was removed under reduced pressure and the residue was partitioned between 1M aqueous NaOH and ethyl acetate. The phases were separated and the aqueous phase was extracted with ethyl acetate twice, and the ethyl acetate phase was added to the organic phase. Extractive workup, drying over Na$_2$SO$_4$, filtration, concentration, and purification by silica gel column chromatography (hexane/ethyl acetate=5/1 as eluent) were performed to furnish compound (1a) as white solid in 82% yield.

In addition, compounds (1b) to (1d) were obtained as white solids in the same manner.

HCl salt of the compound (1a) (0.58 g, 2 mmol) and NaN$_3$ (0.65 g, 10 mmol) were added to 10 mL of trifluoroacetate (TFA) portionwise carefully at 0° C. The resulting mixture was stirred for 6 hours at room temperature and poured into crashed ice with stirring. After neutralization with NaOH pellet, extractive workup was performed with ethyl acetate twice, and the ethyl acetate phase was added to the organic phase. The combined organic phase was washed with brine and dried over Na$_2$SO$_4$. Filtration and concentration of the organic phase gave the crude residue, which was used to next reaction without further purification.

The crude residue was dissolved to 10 mL of MeOH containing 2 mmol of AcOH, and the mixture was cooled to 0° C. in Ar gas atmosphere. 5% Pd/C (0.20 g) was added and the atmosphere was replaced with H$_2$ (balloon). After 1 hour stirring at room temperature, Pd/C was removed by filtration and the filtrate was concentrated. The residue was neutralized by 1M aqueous NaOH and extracted with ethyl acetate twice, and ethyl acetate phase was added to organic extracts. The combined organic extracts were dried over Na$_2$SO$_4$, filtered, and concentrated. Purification by silica gel column chromatography (methanol/ethyl acetate=1/30) afforded 1,2-diamine (2a) as white solid in 89% yield. In addition, 1,2-diamines (2b) to (2d) were obtained as white solids in the same manner except using compounds (1b) to (1d).

Figure 2:
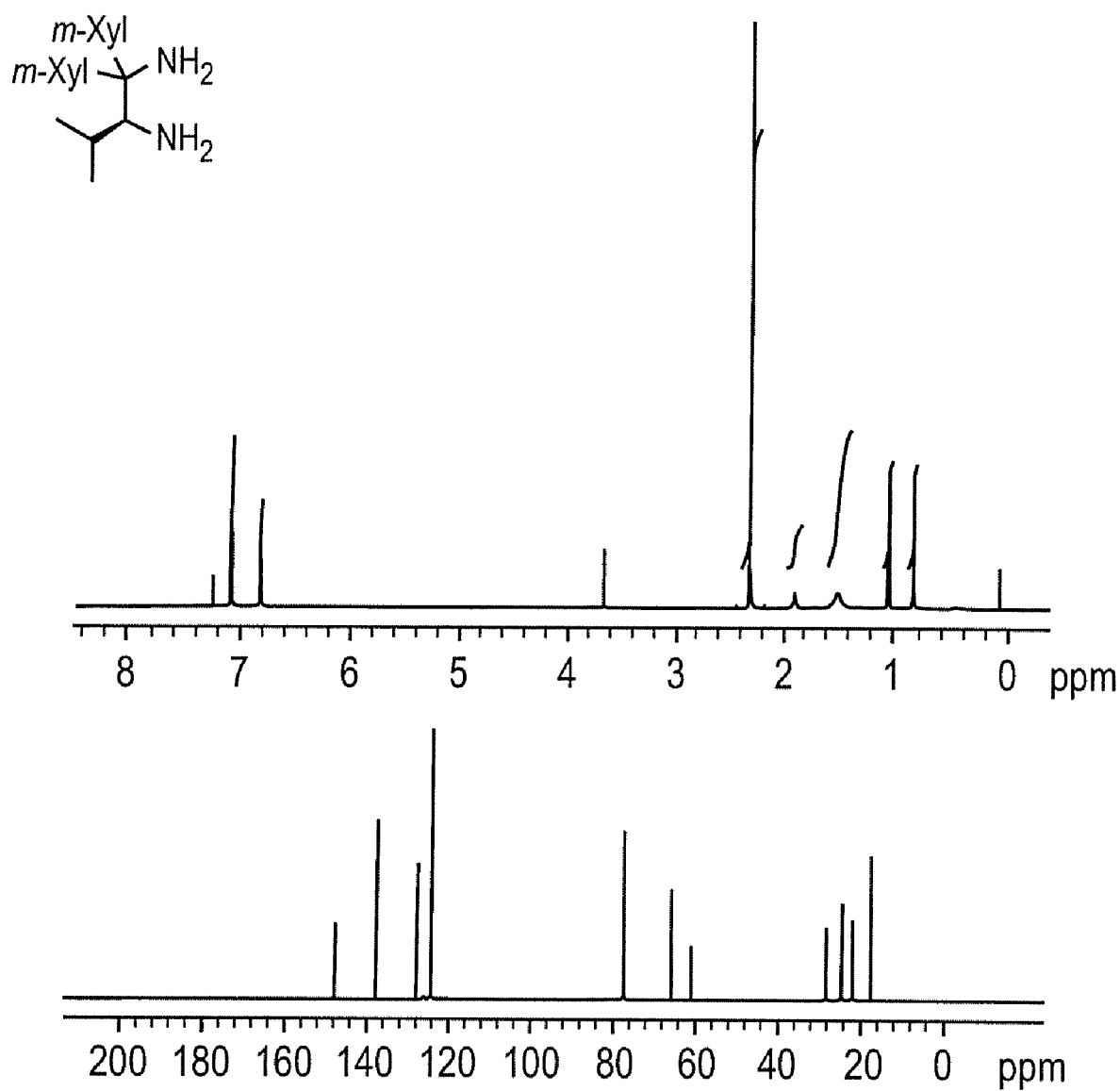
FIG. 2 shows $^1$H and $^{13}$C NMR spectra of 1,2-diamine (2b).
Figure 3:
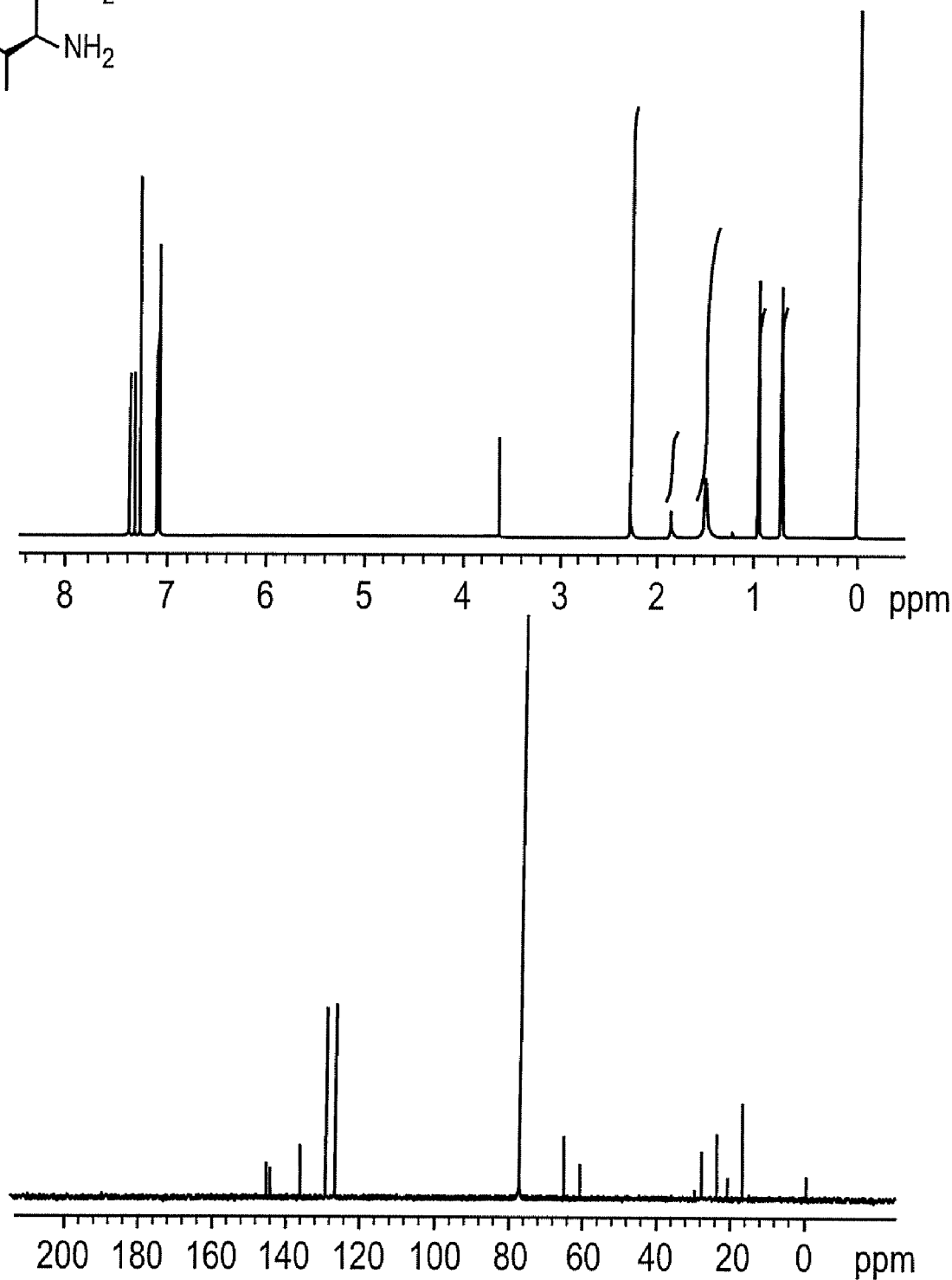
FIG. 3 shows $^1$H and $^{13}$C NMR spectra of 1,2-diamine (2c).
Figure 4:
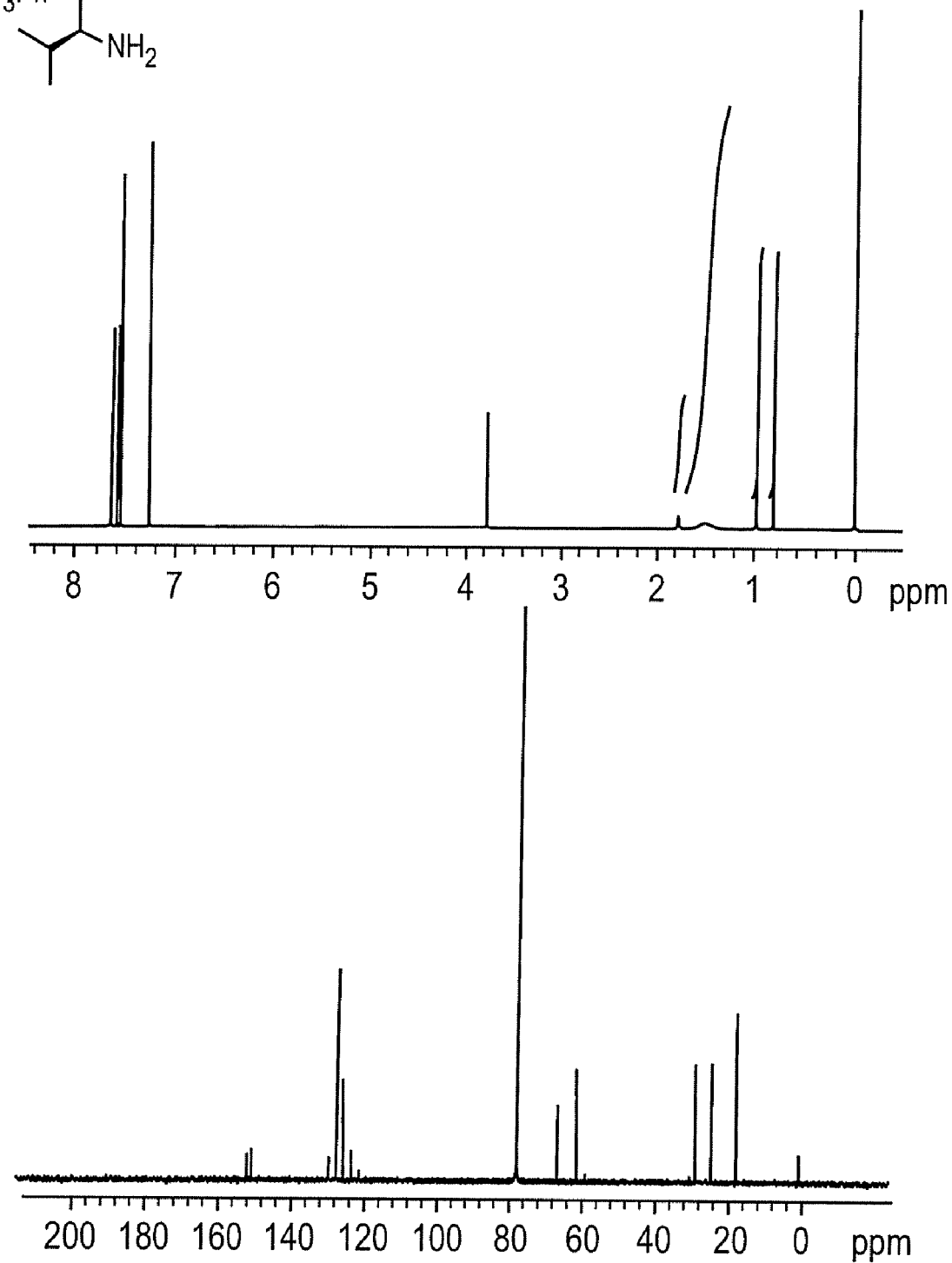
FIG. 4 shows $^1$H and $^{13}$C NMR spectra of 1,2-diamine (2d).

$^1$H and $^{13}$C NMR spectra of 1,2-diamines (2a) to (2d) are shown in FIGS. 1 to 4.

1,2-diamine (2a):
[1] $^1$H-NMR (500 MHz, CDCl$_3$); d7.48 (2H, d, J=7.5 Hz), 7.45 (2H, d, J=7.5 Hz), 7.29 (4H, t, J=7.5 Hz), 7.20 (1H, tt, J=7.5, 2.0 Hz), 7.18 (1H, tt, J=7.5, 2.0 Hz), 3.70 (1H, d, J=2.0 Hz), 1.89 (1H, quin-d, J=7.0, 2.0 Hz), 1.01 (3H, d, J=7.0 Hz), 0.75 (3H, d, J=7.0 Hz),
[2] $^{13}$C-NMR (126 MHz, CDCl$_3$); d148.0, 147.3, 128.4, 128.3, 126.8, 126.3$_8$, 126.3$_2$, 66.0, 60.9, 28.1, 24.1, 17.1,
[3] IR(KBr); 3339, 3275, 2965, 2925, 1598, 1449, 1357, 1188, 1057, 945, 872, 745 cm$^{-1}$,
[4] HRMS(FAB); Calcd for ([M]$^+$) 255.1861. Found 255.1857,
[5] [a]$^{25}{}_D$; +11.0° (c=0.40, MeOH, >99% ee)

1,2-diamine (2b):
[1] $^1$H-NMR (500 MHz, CDCl$_3$); d7.09 (2H, s), 7.07 (2H, s), 6.81 (1H, s), 6.80 (1H, s), 3.63 (1H, d, J=1.5 Hz), 2.28 (6H, s), 2.27 (6H, s), 1.86 (1H, quin-d, J=7.0, 1.5 Hz), 1.00 (3H, d, J=7.0 Hz), 0.77 (3H, d, J=7.0 Hz),
[2] $^{13}$C-NMR (126 MHz, CDCl$_3$); d147.7, 147.3, 137.6, 137.5, 128.0, 127.9, 124.5, 124.4, 65.8, 60.9, 28.0, 24.3, 21.7$_3$, 21.7$_1$, 17.3,
[3] IR(KBr); 3403, 2975, 2867, 1599, 1464, 1369, 1300, 1172, 1038, 864 cm$^{-1}$,
[4] HRMS(FAB); Calcd for ([M]$^+$) 311.2487. Found 311.2501,
[5] [a]$^{24}{}_D$; +26.4° (c=0.41, MeOH, >99% ee)

1,2-diamine (2c):
[1] $^1$H-NMR (500 MHz, CDCl$_3$); d7.36 (2H, d, J=8.5 Hz), 7.33 (2H, d, J=8.5 Hz), 7.09 (4H, d, J=8.5 Hz), 3.63 (1H, d, J=2.0 Hz), 2.29$_4$ (3H, s), 2.28$_6$ (3H, s), 1.87 (1H, quin-d, J=7.0, 2.0 Hz), 0.99 (3H, d, J=7.0 Hz), 0.75 (3H, d, J=7.0 Hz),
[2] $^{13}$C-NMR (126 MHz, CDCl$_3$); d144.8, 144.0, 136.0$_1$, 135.9$_9$, 129.2, 129.0, 126.7, 126.6, 65.5, 61.0, 28.0, 24.1, 21.0, 17.1,
[3] IR(KBr); 3289, 2949, 2875, 1589, 1507, 1452, 1369, 1204, 1023, 945, 893 cm$^{-1}$,
[4] HRMS(FAB); Calcd for ([M]$^+$) 283.2174. Found 283.2181,
[5] [a]$^{23}{}_D$; +25.6° (c=0.43, MeOH, >99% ee)

1,2-diamine (2d):
[1] $^1$H-NMR (500 MHz, CDCl$_3$); d7.65 (2H, d, J=8.0 Hz), 7.59 (2H, d, J=8.0 Hz), 7.55 (4H, d, J=8.0 Hz), 3.77 (1H, d, J=2.0 Hz), 1.78 (1H, quin-d, J=7.0, 2.0 Hz), 0.98 (3H, d, J=7.0 Hz), 0.81 (3H, d, J=7.0 Hz),
[2] $^{13}$C-NMR (126 MHz, CDCl$_3$); d151.6, 150.6, 129.0$_1$ (q, J$_{F-C}$=32.6 Hz), 128.9$_5$ (q, J$_{F-C}$=32.5 Hz), 127.2, 127.0, 125.5$_2$ (q, J$_{F-C}$=3.7 Hz), 125.4$_5$ (q, J$_{F-C}$=3.7 Hz), 124.2 (q, J$_{F-C}$=272.5 Hz), 65.9, 60.6, 28.3, 24.0, 17.2,
[3] $^{19}$F-NMR (282 MHz, CDCl$_3$); d-62.8$_6$, -62.8$_9$,
[4] IR(KBr); 3344, 2977, 2870, 1612, 1412, 1314, 1106, 1012, 950, 854 cm$^{-1}$,
[5] HRMS(FAB); Calcd for ([M]$^+$) 391.1609. Found 391.1607,
[6] [a]$^{25}{}_D$; +6.30 (c=4.9, MeOH, >99% ee)

To a solution of 0.51 g of diamine (2a) (2 equiv, 2.0 mmol) and Et$_3$N (0.70 mL, 5.0 mmol) was added toluene (5.0 mL). Then, the solution was added to a solution of PCl$_5$ (0.21 g, 1.0 mmol) in toluene (5.0 mL) and the reaction mixture was stirred at 110° C. for 2 hours. After evaporation of all volatiles, the residual solid was dissolved into chloroform and washed with 1N aqueous HCl. The organic phase was dried over Na$_2$SO$_4$. Concentration and purification of the residue by column chromatography on silica gel gave tetraaminophosphonium salt (3a) as a mixture of diastereomers (92%, MS:PS=6:1). (M,S)-tetraaminophosphonium salt (3a) was obtained in an essentially pure form by recrystallization from acetone/hexane solvent system at −15° C.

In addition, (M,S)-tetraaminophosphonium salts (3b) to (3d) were obtained in the same manner except using 1,2-diamines (2b) to (2d).

Figure 5:
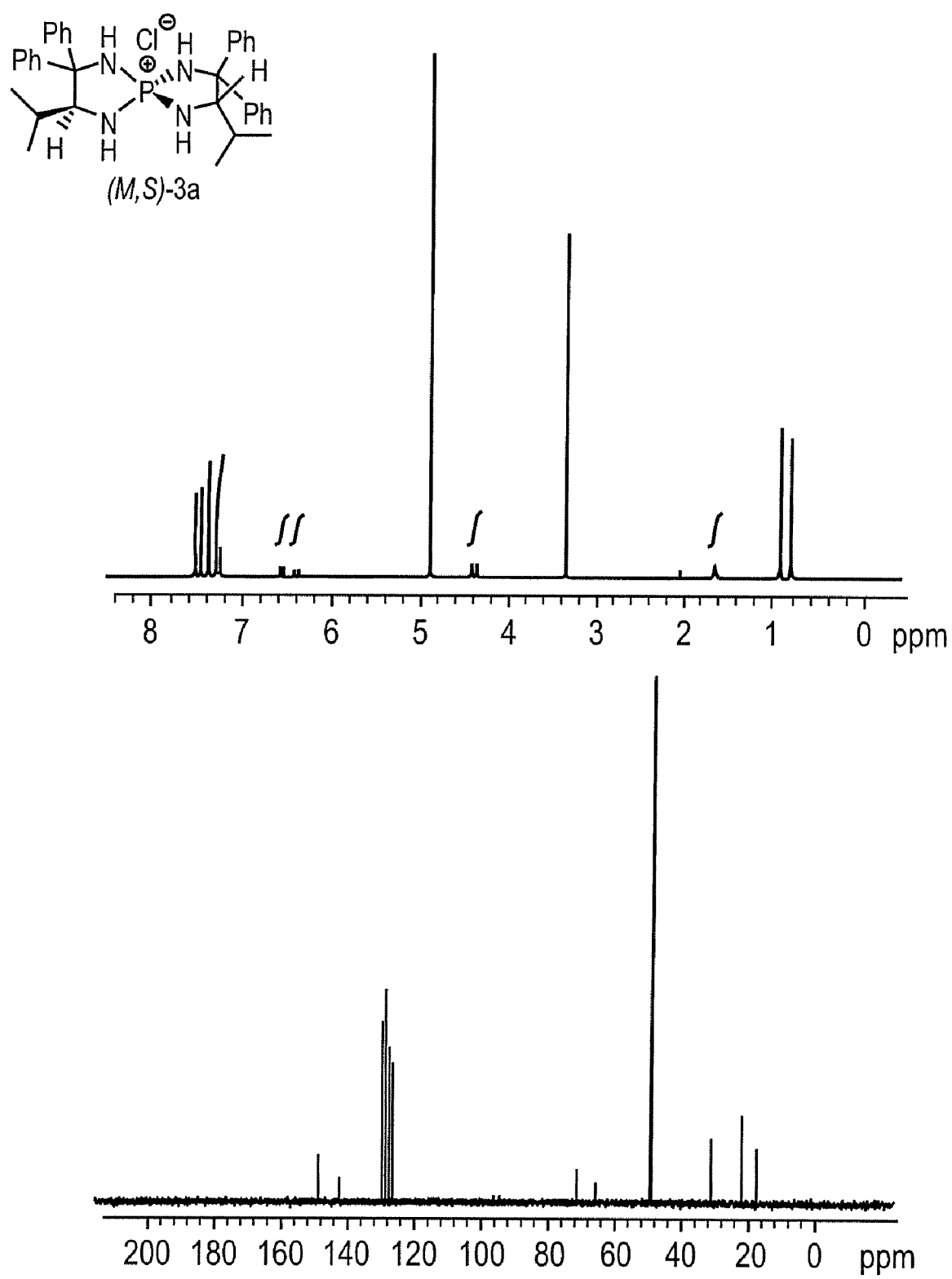
FIG. 5 shows $^1$H and $^{13}$C NMR spectra of (M,S)-tetraaminophosphonium salt (3a).
Figure 6:
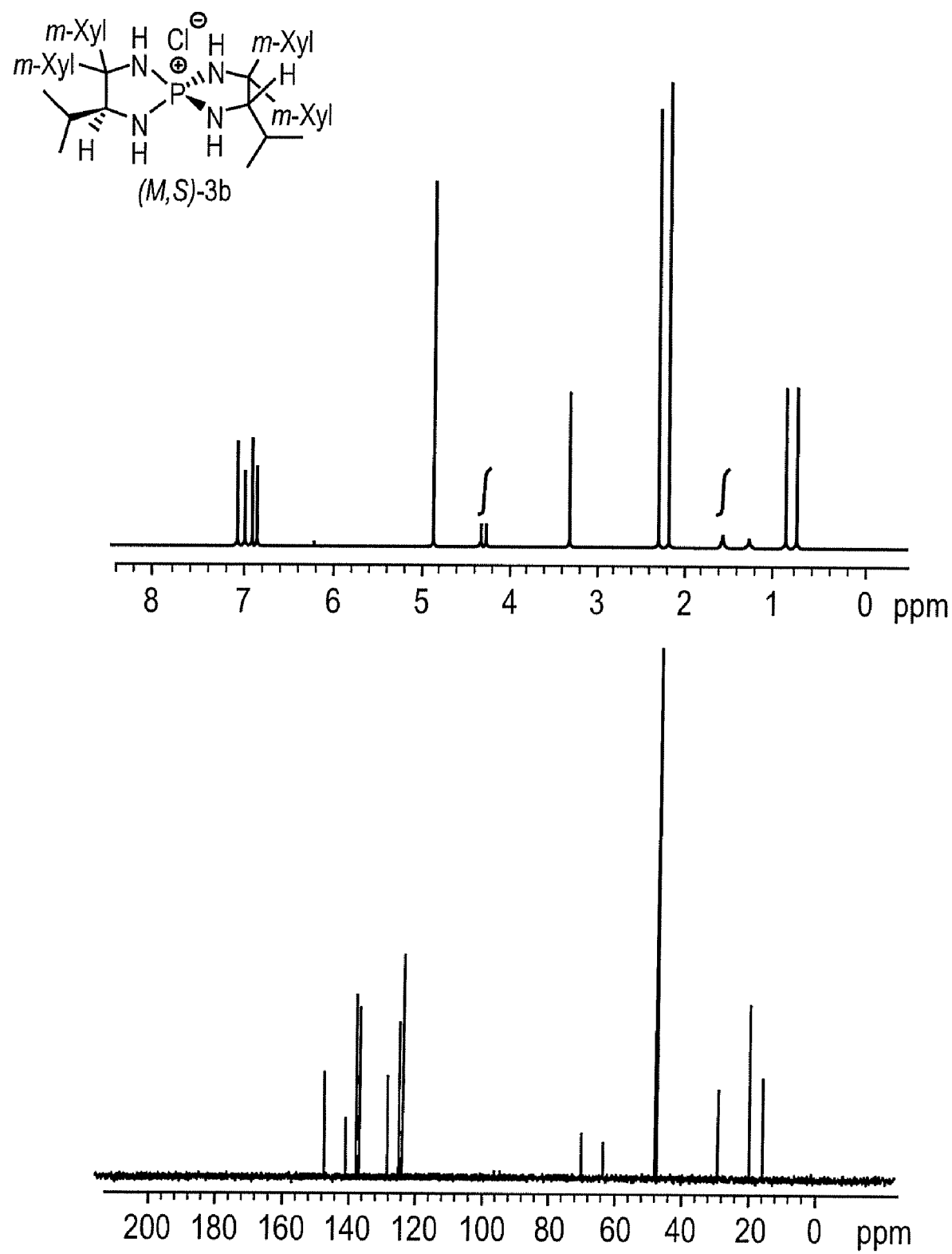
FIG. 6 shows $^1$H and $^{13}$C NMR spectra of (M,S)-tetraaminophosphonium salt (3b).
Figure 7:
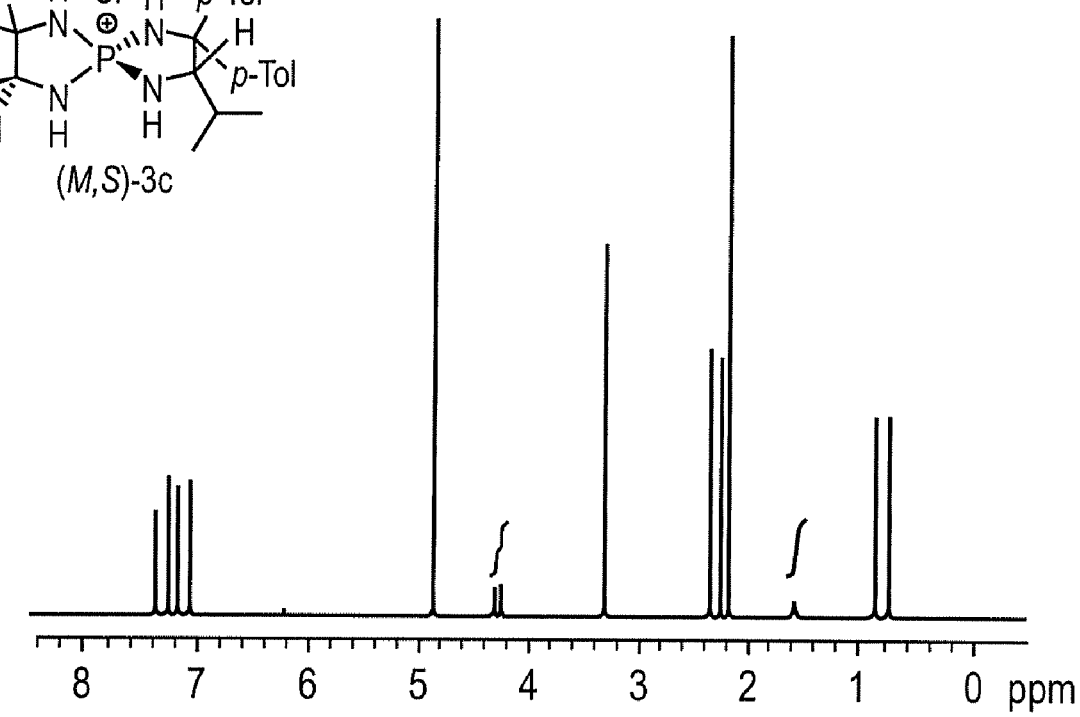
FIG. 7 shows $^1$H and $^{13}$C NMR spectra of (M,S)-tetraaminophosphonium salt (3c).
Figure 8:
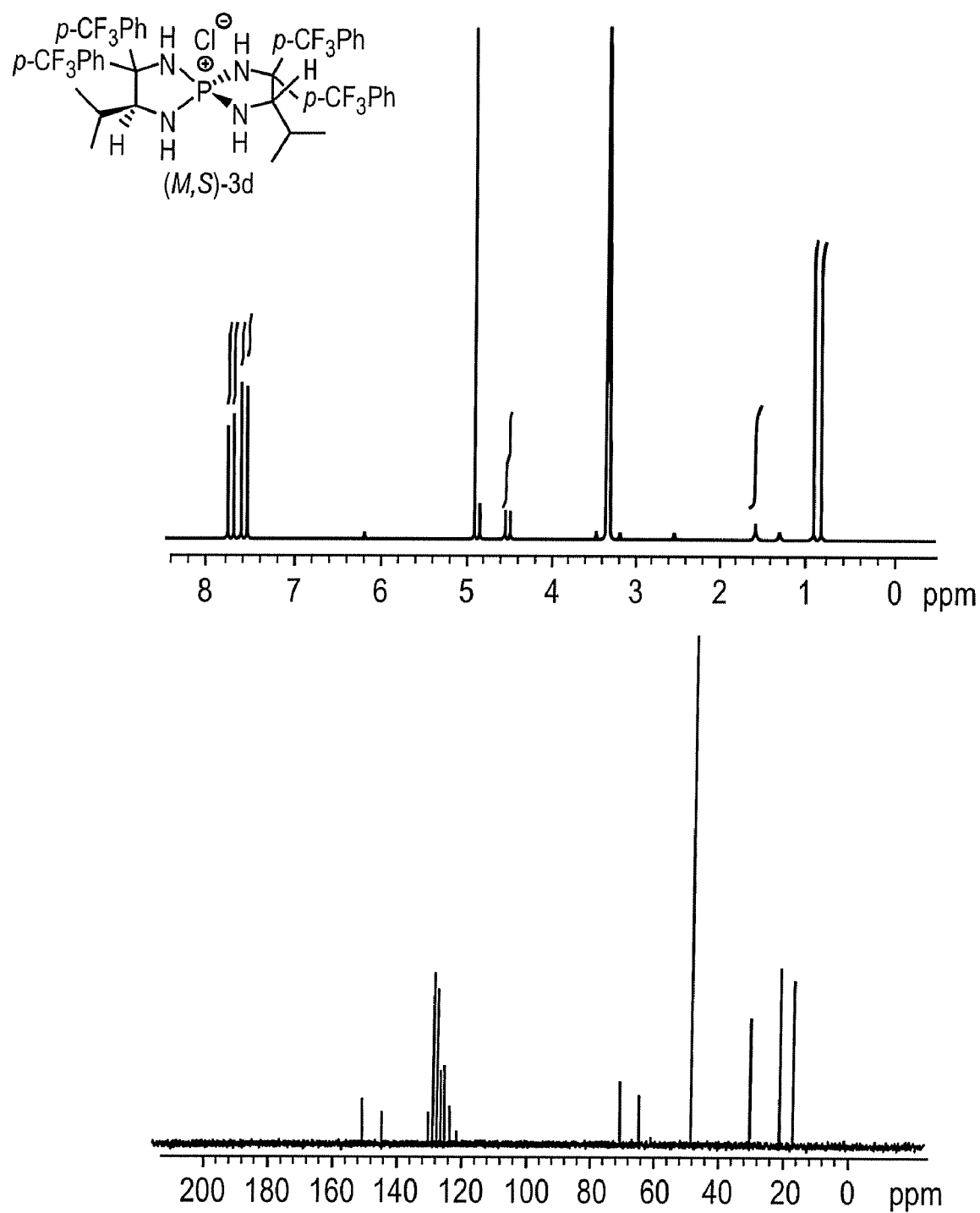
FIG. 8 shows $^1$H and $^{13}$C NMR spectra of (M,S)-tetraaminophosphonium salt (3d).

$^1$H and $^{13}$C NMR spectra of (M,S)-tetraaminophosphonium salts (3a) to (3d) are shown in FIGS. 5 to 8.

(M,S)-(3a):

[1] $^1$H-NMR (500 MHz, CD$_3$OD); d7.48 (4H, d, J=7.5 Hz), 7.42 (4H, t, J=7.5 Hz), 7.33 (2H, tt, J=7.5, 1.8 Hz), 7.31 (4H, d, J=7.5 Hz), 7.24 (4H, t, J=7.5 Hz), 7.19 (2H, tt, J=7.5, 2.0 Hz), 6.50 (2H, d, $J_{P-H}$=18.0 Hz), 6.34 (2H, d, $J_{P-H}$=21.0 Hz), 4.35 (2H, dd, $J_{P-H}$=24.0 Hz, $J_{H-H}$=3.5 Hz), 1.61 (2H, quin-d, J=6.8, 3.5 Hz), 0.88 (6H, d, J=6.8 Hz), 0.77 (6H, d, J=6.8 Hz),

[2] $^{13}$C-NMR (126 MHz, CD$_3$OD); d148.5, 142.2 (d, $J_{P-C}$=12.3 Hz), 129.7, 128.9, 128.6, 128.3$_0$, 128.2$_7$, 127.6, 71.6 (d, $J_{P-C}$=12.8 Hz), 65.6 (d, $J_{P-C}$=7.7 Hz), 30.9, 21.7, 17.5,

[3] $^{31}$P-NMR (121 MHz, CD$_3$OD); d35.8,

[4] IR(KBr); 3385, 3185, 2963, 1609, 1461, 1400, 1338, 1260, 1126, 1056, 759, 702 cm$^{-1}$,

[5] HRMS(FAB); Calcd for C$_{34}$H$_{40}$N$_4$P$^+$([M]$^+$) 535.2991. Found 535.3011,

[6] [a]$^{28}$$_D$; −297.1° (c=0.32, CH$_3$OH, >99% ee)

(M,S)-(3b);

[1] $^1$H-NMR (500 MHz, CD$_3$OD); d7.05 (4H, s), 6.96 (2H, s), 6.87 (4H, s), 6.84 (2H, s), 6.31 (2H$_{(partially\ deuterated)}$, d, $J_{P-H}$=17.5 Hz), 4.28 (2H, dd, $J_{P-H}$=24.5 Hz, $J_{H-H}$=3.5 Hz), 2.32 (12H, s), 2.21 (12H, s), 1.59 (2H, quin-d, J=7.0, 3.5 Hz), 0.88 (6H, d, J=7.0 Hz), 0.75 (6H, d, J=7.0 Hz),

[2] $^{13}$C-NMR (126 MHz, CD$_3$OD); d148.6, 142.2 (d, $J_{P-C}$=11.9 Hz), 139.2, 138.5, 129.8, 129.6, 126.1, 125.3, 71.4 (d, $J_{P-C}$=12.4 Hz), 64.8 (d, $J_{P-C}$=8.3 Hz), 30.8, 21.8$_1$, 21.7$_9$, 21.7$_7$, 21.5, 21.4, 17.7,

[3] $^{31}$P-NMR (121 MHz, CD$_3$OD); d35.0,

[4] IR(KBr); 3350, 3166, 2954, 1604, 1462, 1392, 1166, 1070, 852, 737, 700 cm$^{-1}$,

[5] HRMS(FAB); Calcd for C$_{42}$H$_{56}$N$_4$P$^+$([M]$^+$) 647.4243. Found 647.4255,

[6] [a]$^{23}$$_D$; −303.2° (c=0.39, CH$_3$OH, >99% ee)

(M,S)-(3c);

[1] $^1$H-NMR (500 MHz, CD$_3$OD); d7.34 (4H, d, J=8.5 Hz), 7.23 (4H, d, J=8.0 Hz), 7.16 (4H, d, J=8.5 Hz), 7.04 (4H, d, J=8.0 Hz), 4.24 (2H, dd, $J_{P-H}$=24.0 Hz, $J_{H-H}$=3.5 Hz), 2.36 (6H, s), 2.26 (6H, s), 1.60 (2H, quin-d, J=6.8, 3.5 Hz), 0.87 (6H, d, J=6.8 Hz), 0.74 (6H, d, J=6.8 Hz),

[2] $^{13}$C-NMR (126 MHz, CD$_3$OD); d145.7, 139.4 (d, $J_{P-C}$=11.9 Hz), 138.4, 138.1, 130.2, 129.5, 128.2, 127.5, 71.1 (d, $J_{P-C}$=12.8 Hz), 65.7 (d, $J_{P-C}$=8.2 Hz), 30.8, 21.7, 20.9$_3$, 20.8$_8$, 17.6,

[3] $^{31}$P-NMR (121 MHz, CD$_3$OD); d35.1,

[4] IR(KBr); 3150, 2954, 1621, 1512, 1403, 1330, 1268, 1198, 1136, 1054, 926, 813 cm$^{-1}$,

[5] HRMS(FAB); Calcd for C$_{38}$H$_{48}$N$_4$P$^+$([M]$^+$) 591.3617. Found 591.3592,

[6] [a]$^{23}$$_D$; −231.9° (c=0.34, CH$_3$OH, >99% ee)

(M,S)-(3d);

[1] $^1$H-NMR (500 MHz, CD$_3$OD); d7.75 (4H, d, J=8.0 Hz), 7.68 (4H, d, J=8.5 Hz), 7.60 (4H, d, J=8.5 Hz), 7.53 (4H, d, J=8.0 Hz), 4.48 (2H, dd, $J_{P-H}$=25.0 Hz, $J_{H-H}$=3.5 Hz), 1.59 (2H, quin-d, J=6.5, 3.5 Hz), 0.90 (6H, d, J=6.5 Hz), 0.82 (6H, d, J=6.5 Hz),

[2] $^{13}$C-NMR (126 MHz, CD$_3$OD); d151.9, 145.8 (d, $J_{P-C}$=12.8 Hz), 131.1 (q, $J_{F-C}$=32.3 Hz), 130.9 (q, $J_{F-C}$=32.4 Hz), 129.3, 128.3, 126.9, 126.0, 125.7 (q, $J_{F-C}$=313.5 Hz), 125.4 (q, $J_{F-C}$=271.0 Hz), 71.4 (d, $J_{P-C}$=13.2 Hz), 65.4 (d, $J_{P-C}$=8.3 Hz), 31.1, 21.6, 17.3,

[3] $^{31}$P-NMR (121 MHZ, CD$_3$OD); d38.6,

[4] $^{19}$F-NMR (282 MHz, CD$_3$OD); d-62.2, −62.3,

[5] IR(KBr); 3193, 1619, 1479, 1409, 1327, 1268, 1172, 1126, 1070, 1016, 841 cm$^{-1}$,

[6] HRMS(FAB); Calcd for C$_{38}$H$_{36}$F$_{12}$N$_4$P$^+$([M]$^+$) 807.2486. Found 807.2492,

[7] [a]$^2$$_D$; −226.7° (c=1.01, CH$_3$OH, >99% ee)

2. Synthesis of Chiral Tetraaminophosphonium Salt (II)

Figure 9:
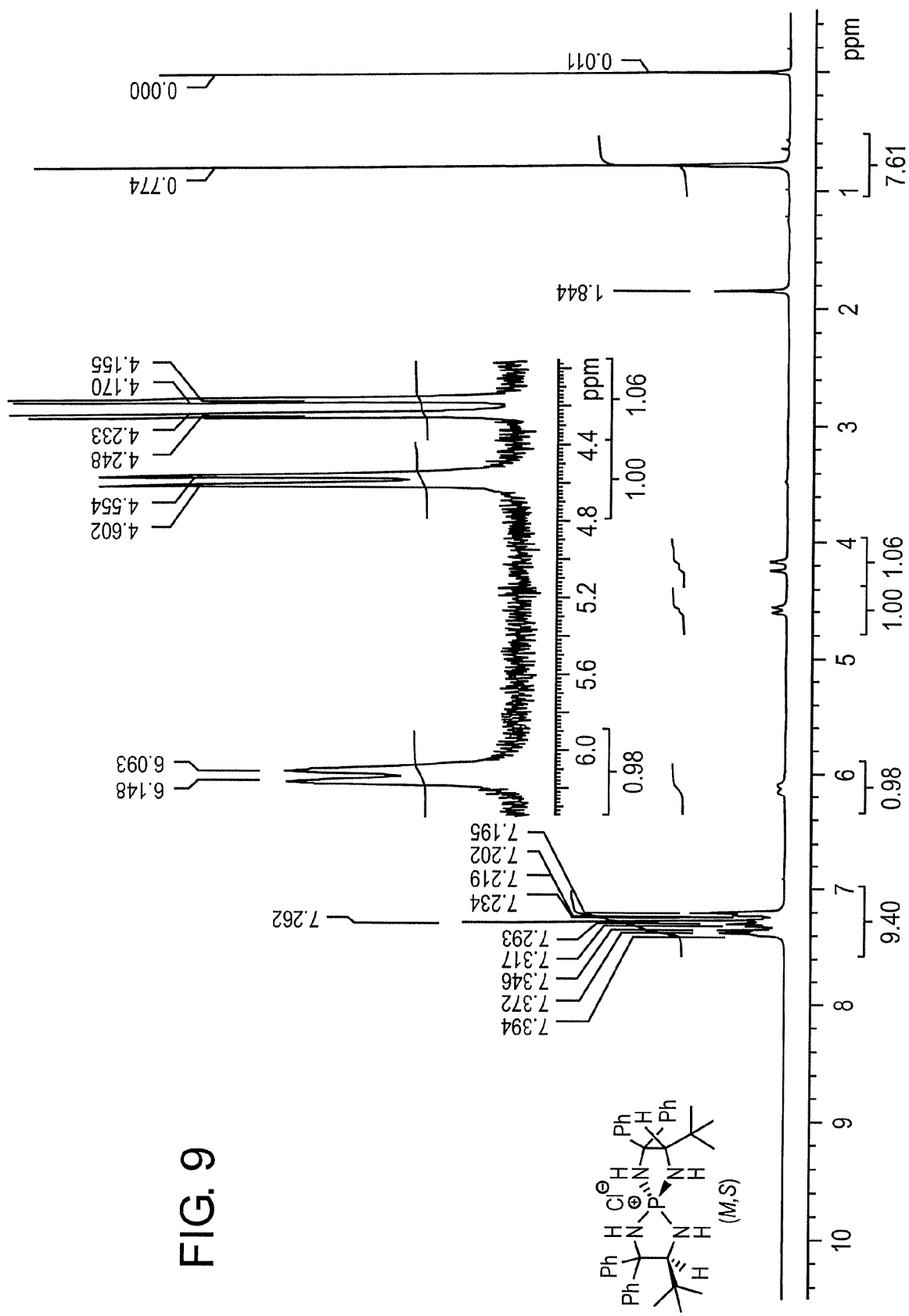
FIG. 9 shows $^1$H and $^{13}$C NMR spectra of (M,S)-tetraaminophosphonium salt (3e).
Figure 10:
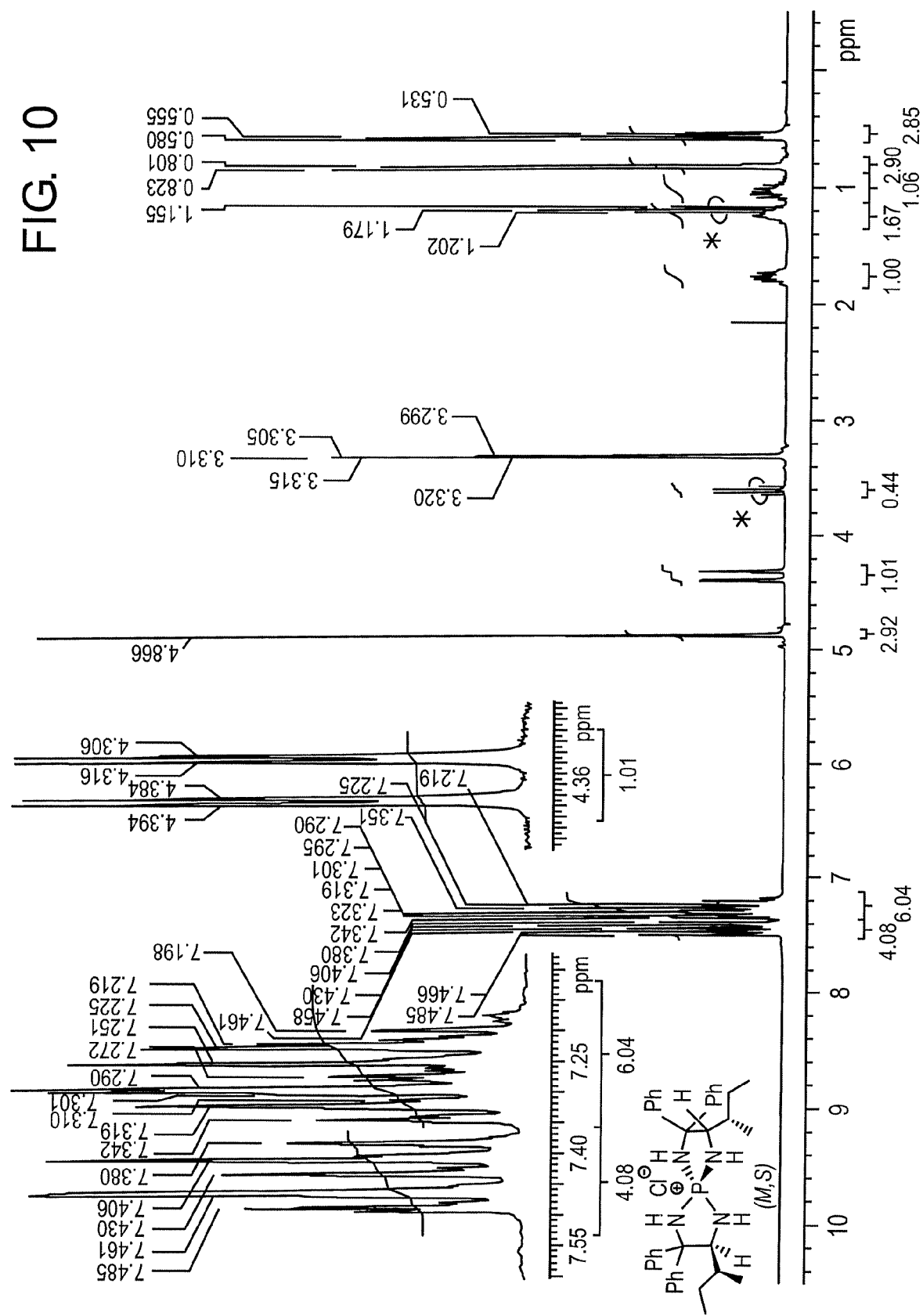
FIG. 10 shows $^1$H and $^{13}$C NMR spectra of (M,S)-tetraaminophosphonium salt (3f).
Figure 11:
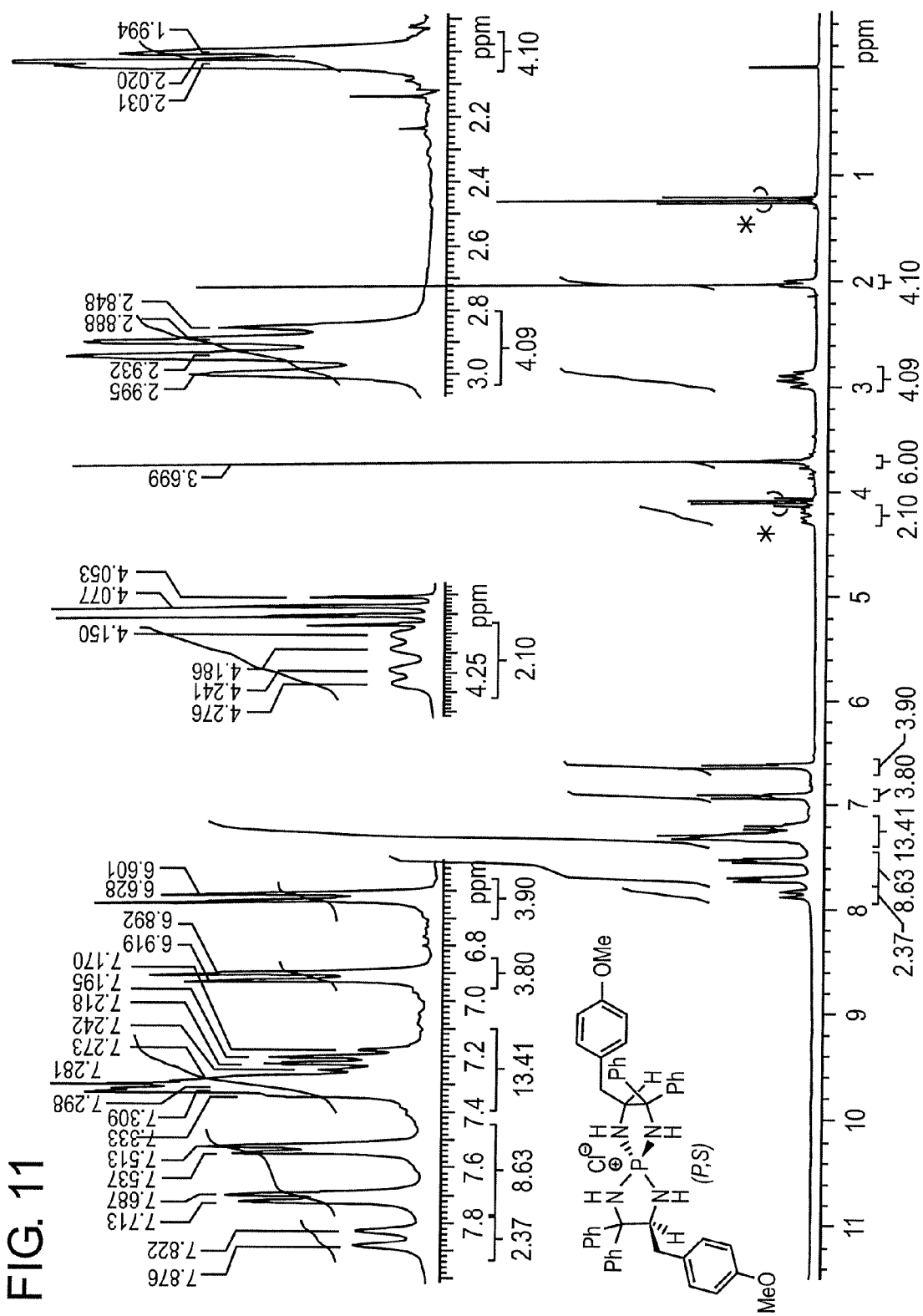
FIG. 11 shows $^1$H and $^{13}$C NMR spectra of (P,S)-tetraaminophosphonium salt (3g).
Figure 12:
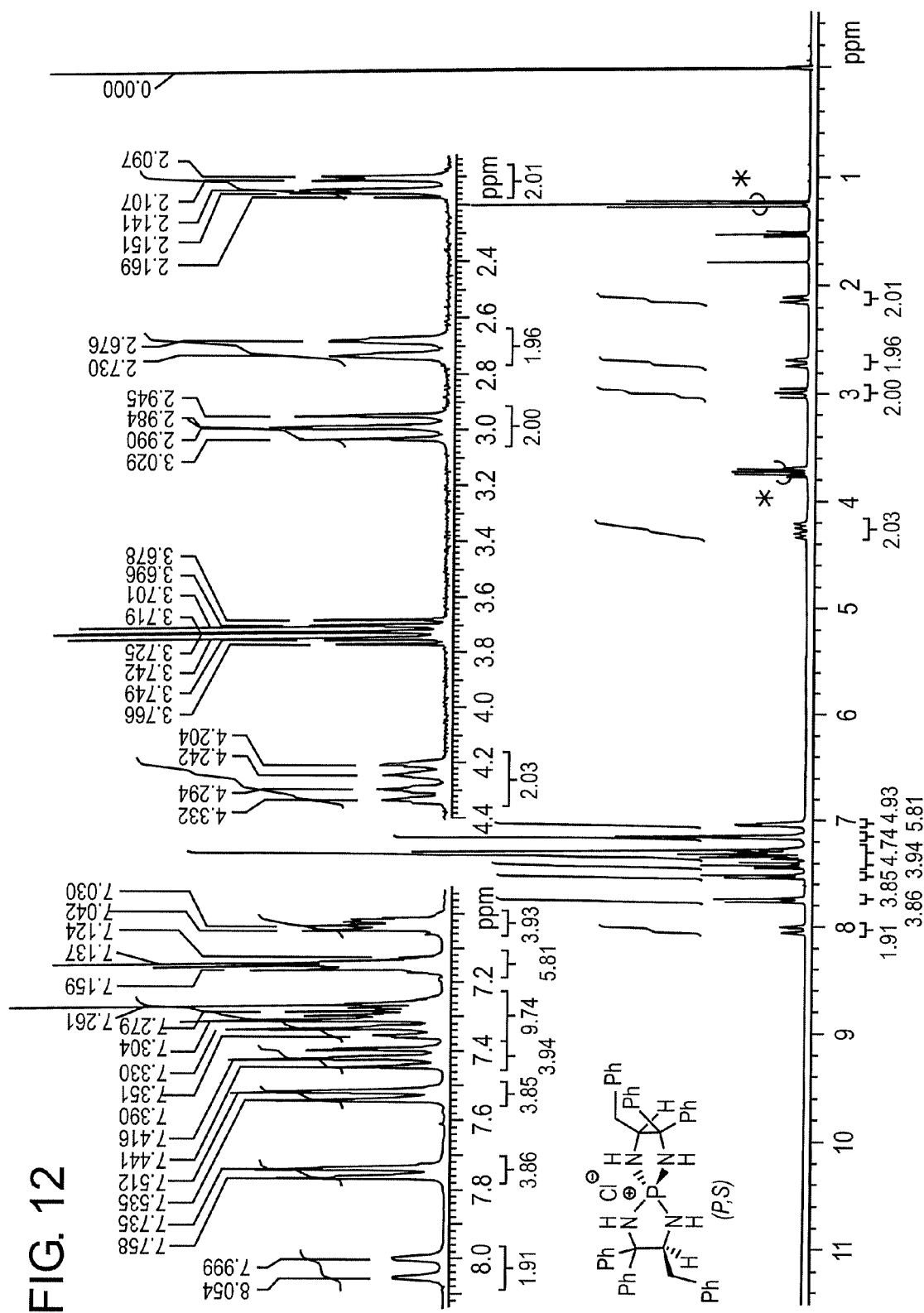
FIG. 12 shows $^1$H and $^{13}$C NMR spectra of (P,S)-tetraaminophosphonium salt (3h).

Chiral tetraaminophosphonium salts (3e) to (3h) were obtained in the same manner as in synthesis (I) above. The chiral tetraaminophosphonium salts (3e) and (3f) were (M,S) isomers, and (3g) and (3h) were (P, S) isomers. $^1$H NMR spectra of tetraaminophosphonium salts (3e) to (3h) are shown in FIGS. 9 to 12. In FIGS. 9 to 12, "*" indicates peak originated from residual ethanol.

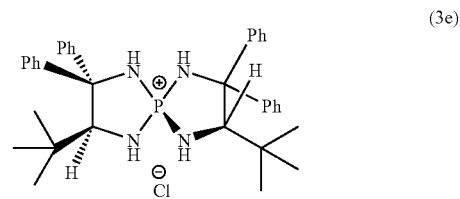

(3e)

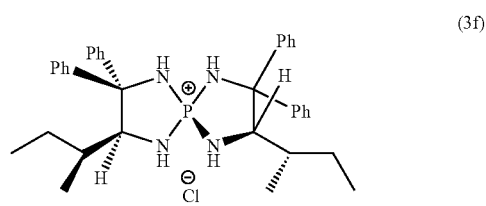

(3f)

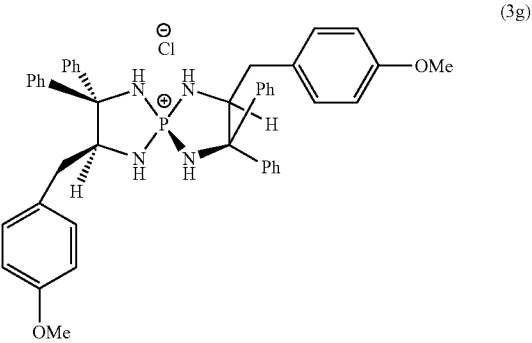

(3g)

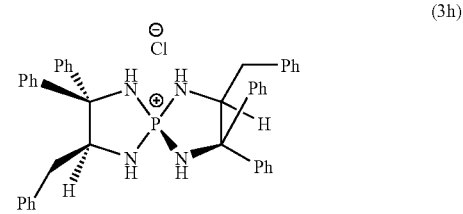

(3h)

3. Synthesis of β-Nitroalcohol (I)

Benzaldehyde was used as the aldehyde. Nitroalkanes (4a) to (4c) having monovalent hydrocarbon group (R$^9$) shown in Table 1 were used as the nitroalkane. And (M,S)-tetraaminophosphonium salts (3a) to (3d) were used as the tetraaminophosphonium salt. Using these materials, β-nitroalcohols were synthesized by the method described below. Yields, diastereomer ratios, and enantiomeric excess for the resulting β-nitroalcohols were measured. The results are shown in Table 1.

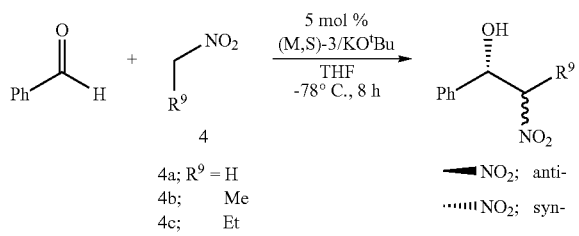
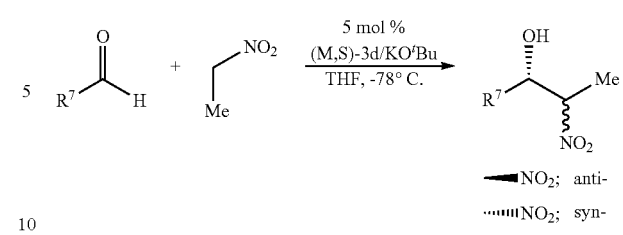

In Ar gas atmosphere, (M,S)-tetraaminophosphonium salt (3a) (0.055 equiv, 13.75 μmol) was dissolved in THF (2.5 mL) containing nitroalkane (4) (10.0 equiv, 2.5 mmol) at room temperature. Subsequently, 12.5 μmol of potassium-t-butoxide solution (1.0 M, THF solvent) was added, and the reaction solution was stirred at −78° C. for 30 min. After that, benzaldehyde (1.0 equiv, 0.25 mmol) was gradually added dropwise to the reaction solution, and stirring was continued for 8 hours. Toluene (0.5 M., 100 μL) containing TFA was added to the reaction solution, and the solution was then poured into water chilled on ice. The organic layer and aqueous layer were separated, and the aqueous layer was extracted by ethyl acetate, whereupon the ethyl acetate layer was added to the organic layer. The organic layer was dried over $Na_2SO_4$ and filtered. The entire volatile content was distilled off to obtain a crude residue, and the crude residue was purified by silica gel column chromatography to obtain β-nitroalcohol. The diastereomer ratio of the resulting β-nitroalcohol was measured by subjecting the crude residue to $^1$H-NMR analysis. In addition, the resulting β-nitroalcohol enantiomeric excess was determined by HPLC analysis using a chiral column (diameter 4.6 mm×250 mm, "CHIRALCEL OD-H" or "CHIRALPAK AD-H" manufactured by DAICEL).

TABLE 1

| Entry | (M,S)-3 | 4($R^9$) | Yield*[1] (%) | dr*[2] (anti:syn) | ee*[3] (%) |
|---|---|---|---|---|---|
| 1 | 3a | 4a | 86 | | 89 |
| 2 | 3b | 4a | 36 | | 45 |
| 3 | 3c | 4a | 84 | | 88 |
| 4 | 3d | 4a | 90 | | 94 |
| 5 | 3d | 4b | 93 | >19:1 | 97 |
| 6 | 3d | 4c | 78 | 13:1 | 96 |
| 7*[4] | 3d | 4b | 90 | >19:1 | 97 |

*[1]Isolated yield
*[2]Determined by $^1$H NMR analysis of crude reaction mixtures.
*[3]Enantiomeric excess of anti-isomer determined by chiral HPLC analysis. (entries 5-7).
*[4]Reaction was performed for 48 hours with 1 mol % of (M,S)-3d/KO$^t$Bu.

4. Synthesis of β-nitroalcohol (II)

The aldehyde having the monovalent hydrocarbon group ($R^7$) shown in Table 2 were used as the aldehyde. In addition, nitroethane was used as the nitroalkane, and (M,S)-tetraaminophosphonium salt (3d) was used as the tetraaminophosphonium salt. These materials were used to synthesize β-nitroalcohols in the same manner. However, the reaction time was changed in accordance with the aldehyde substrate. The reaction times are shown in Table 2. Yields, diastereomer ratios and enantiomeric excess for the resulting β-nitroalcohols were measured. The results are shown in Table 2. The methods for measuring the diastereomer ratio and enantiomeric excess are the same as described above.

TABLE 2

| Entry | $R^7$ | Reaction time (h) | Yield*[1] (%) | dr*[2] (anti:syn) | ee*[3] (%) |
|---|---|---|---|---|---|
| 1 | o-F—$C_6H_4$ | 5 | 94 | >19:1 | 96 |
| 2 | p-F—$C_6H_4$ | 9 | 91 | >19:1 | 97 |
| 3 | p-Cl—$C_6H_4$ | 9 | 95 | >19:1 | 97 |
| 4 | p-Me-$C_6H_4$ | 24 | 90 | >19:1 | 97 |
| 5 | 1-Naphthyl | 8 | 84 | >19:1 | 96 |
| 6 | 2-Furyl | 6 | 96 | >19:1 | 97 |
| 7 | (E)-PhCH=CH | 21 | 74 | >19:1 | 99 |
| 8 | Ph($CH_2$)$_2$ | 24 | 76 | 4:1 | 93 |
| 9 | Me($CH_2$)$_7$ | 24 | 77 | 4:1 | 94 |

*[1]Isolation yield
*[2]Measured by $^1$H-NMR of the crude reaction mixture
*[3]Enantiomeric excess of anti-isomer determined by chiral HPLC analysis.

5. Synthesis of β-Nitroalcohol (III)

Pyruvic acid methyl ester was used instead of the aldehyde to synthesize β-nitroalcohol in the same manner as in section (4) above. The results gave a yield of 24%, a diastereoselectivity (anti-form/syn-form) of 2:1, and a primary product isomer enantioselectivity of 78% ee.

What is claimed is:

1. A chiral tetraaminophosphonium salt represented by the general formula (1):

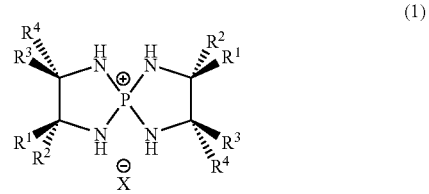

(1)

wherein $R^1$ to $R^4$ are independently a hydrogen atom or a monovalent hydrocarbon group;

and, $R^1$ and $R^2$ are different groups or $R^3$ and $R^4$ are different groups, and wherein $X^-$ is a monovalent or polyvalent anion.

2. The chiral tetraaminophosphonium salt according to claim 1, wherein one of said $R^1$ and $R^2$ is a hydrogen atom and said $R^3$ and $R^4$ are aryl groups.

3. The chiral tetraaminophosphonium salt according to claim 1, which is a chiral tetraaminophosphonium salt represented by the general formula (1-1) or an enantiomer thereof (1-1)

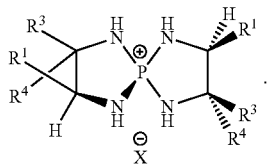

4. The chiral tetraaminophosphonium salt according to claim 1, which is a chiral tetraaminophosphonium salt represented by the general formula (1-2) or an enantiomer thereof (1-2)

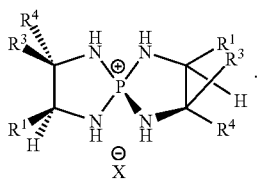

5. A catalyst for asymmetric synthesis comprising a chiral tetraaminophosphonium salt represented by the general formula (1) or a conjugated base thereof:

(1)

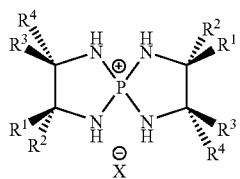

wherein $R^1$ to $R^4$ are independently a hydrogen atom or a monovalent hydrocarbon group;
and, $R^1$ and $R^2$ are different groups or $R^3$ and $R^4$ are different groups, and
wherein $X^-$ is a monovalent or polyvalent anion.

6. The catalyst for asymmetric synthesis according to claim 5, wherein said asymmetric synthesis is a synthesis reaction for chiral β-nitroalcohol.

7. A method for producing chiral β-nitroalcohol, comprising reacting an aldehyde or a ketone and a nitroalkane in the presence of a chiral tetraaminophosphonium salt represented by the general formula (1) and a base, or in the presence of a conjugated base of said chiral tetraaminophosphonium salt:

(1)

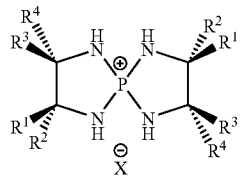

wherein $R^1$ to $R^4$ are independently a hydrogen atom or a monovalent hydrocarbon group;
and, $R^1$ and $R^2$ are different groups or $R^3$ and $R^4$ are different groups, and
wherein $X^-$ is a monovalent or polyvalent anion.

8. The method for producing chiral β-nitroalcohol according to claim 7, wherein said aldehyde or said ketone is a compound represented by the general formula (2), and said nitroalkane is a nitroalkane represented by the general formula (3):

(2)

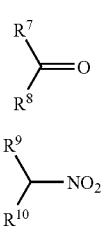

(3)

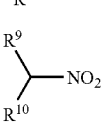

wherein $R^7$ is a monovalent hydrocarbon group; $R^8$ is a hydrogen atom or a monovalent hydrocarbon group; $R^7$ and $R^8$ may bond together to form a ring; $R^9$ and $R^{10}$ are independently a hydrogen atom or a monovalent hydrocarbon group; and $R^9$ and $R^{10}$ may bond together to form a ring.

* * * * *